US007288371B1

(12) United States Patent
Bavykin et al.

(10) Patent No.: US 7,288,371 B1
(45) Date of Patent: Oct. 30, 2007

(54) **DISCRIMINATION OF *BACILLUS ANTHRACIS* FROM CLOSELY RELATED MICROORGANISMS

OTHER PUBLICATIONS

Lander E. S. Array of hope. *Naturet Genet.* (1999) 21 (1 Suppl):3-4. No.

Lechner et al., (1998) *Bacillus weihenstephanensis* sp. *nov.* is a new psychrotolerant species of the *Bacillus cereus* group. *Int. J. Syst. Bacteriol.* 48:1373-1382.

Lee et al., (1999) Fluorescent detection techinques for real-time multiplex strand specific detection of *Bacillus anthracis* using rapid PCR. *J App.l Microbiol.* 87(2):218-23.
Liang and Yu. (1999) Identification of *Bacillus anthracis* strains in China. *J. Appl. Microbiol.* 87:200-203.
Nakamura, L. K. (1998) *Bacillus pseudomycoides* sp. *nov. Int. Syst. Bacteriol.* 48:1031-1034.
Nakamura and Jackson. (1995) Clarification of the taxonomy of *Bacillus mycoides. Int. J. Syst. Bacteriol.* 45:46-49.
Prub et al., (1999) Correlation of 16S ribosomal DNA signature sequences with temperature-dependent growth rates of Mesophilic and Psychrotolerant strains of the *Bacillus cereus* group. *J. Bacteriol.* 181:2624-2630.
Sjostedt et al., (1996) Detection of the vegetative form of *Bacillus anthracis* in soil by PCR. Salisbury Medical Bulletin, Special Supplement No. 87, 50.
Sneath, P. H. A. (1986) Endospore-forming Gram-positive rods and cocci, p. 1104-1139. In J. G. Holt (ed.), Bergey's Manual of Systematic Bacteriology The Williams & Wilkins Co., Baltimore, MD.
Throne, C. B. (1985) Genetics of *Bacillus anthracis*, p. 56-62. In L. Leive (ed.), Microbiology-1985. American Society for Microbiology, Washington, D.C.
Timofeev et al., (1996) Regioselective immobilization of short oligonucleotides to acrylic copolymer gels. *Nucleic Acids Res.* 24(16):3142-8.
Turnbull, P. C. B. (1999) Definitive identification of *Bacillus anthracis*—a review. *J. Appl. Microbiol.* 87:237-240.
Turnbull et al., (1992) *Bacillus anthracis* but not always anthrax. *J. Appl. Bacteriol.* 72;21-28.
Woese, C. R. (1987) Bacterial evolution. *Microbiol. Rev.* 51:221-271.
Website: http://www.cme.msu.edu/RDP Homepage: http://www.cme.msu.edu/ (printed Apr. 4, 2003).
Website: http://www/ebi.ac.uk/clustlaw Homepage: http://www.ebi.ac.uk/ (printed Apr. 4, 2003).
Website: http://www.sciencenet.com/au/bacillaceae.htm (printed Oct. 17, 2002).
Website and Homepage: http://www.tigr.org (printed Apr. 4, 2003).
Ash, Carol and Collins Matthew D. (1992) "Comparative Analysis of 23S Ribosomal RNA Gene Sequences of *Bacillus anthracis* and *Bacillus cereus* Determined by PCR —Direct Sequencing" *FEMS Mircobiology Letters* 94:75-80.
Ash, Carol, et. al. (1991) "Comparative Analysis of *Bacillus anthracis, Bacillus cereus*, and Related Species on the Basis of Reserve Transcriptase Sequencing of 16S rRNA" *International Journal of Systematic Bacteriology* 343-346.
Ash, Carol. et. al. (1991) "Phylogenetic Heterogeneity of the Genus *Bacillus* Revealed by Comparative Analysis of Small-Subunit-Ribosomal RNA Sequences" *Let. Appl. Microbiol.* 202-206.
Bavykin, Sergei G., et. al. (2001) "Portable System for Microbial Sample Preparation and Oligonucleotide Microarray Analysis" *Applied and Environmental Microbiology* 922-928.
Beyer, W., P. Glöckner, J. Otto, and R B Böhm (1996) "A Nested PCR and DNA-Amplification-Fingerprinting Method for Detection and Identification of *Bacillus anthracis* in Soil Samples From Former Tanneries" *Salisbury Medical Bulletin, Special Supplement* No. 87:47-49.
Chee, Mark et. al. (1996) "Accessing Genetic Information with High-Density DNA Arrays" *Science* 274 (5287):610-615.
Daffonchio, Daniele, et. al. (2000) "Homoduplex and Heteroduplex Polymorphisms of the Amplified Ribosomal 16S-23S Internal Transcribed Spacers Describe Genetic Relationships in the *'Bacillus cereus* Group'" *Applied and Environmental Microbiology* 66(12):5460-5468.
Griffel, M.C. te, et. al. (1997) "Discrimination Between *Bacillus thuringiensis* Using Specific DNA Probes Based on Variable Regions of 16S rRNA" *FEMS Microbiology Letters* 146:47-51.
Guschin, Dmitry et. al. (1997) "Manual Manufacturing of Oligonucleotide, DNA, and Protein Microchips" *Analytical Biochemistry* 250:203-211.
Guschin, Dmitry et. al. (1997) "Oligonucleotide Microchips as Genosensors for eterminative and Environmental Studies in Microbiology." *Applied and Environmental Microbiology* 63(6):2397-2402.
Harrell, L.J., et al. .(1995) "Genetic Variability of *Bacillus anthracis* and Related Species." *Journal of Clinical Microbiology* 33(7): 1847-1850.
Helgason, E., et al. (2000) "*Bacillus anthracis, Bacillus cereus*, and *Bacillus thuringiensis*—One Species on the Basis of Genetic Evidence." *Applied and Environmental Microbiology* 66(6):2627-2630.
Henderson, I., et al. (1996) "Fingerprinting *Bacillus anthracis* strains." *Salisbury Medical Bulletin, Special Supplement No.* 87:55-58.
Henderson, I., et al. (1994) "Differentiation of *Bacillus anthracis* from Other *Bacillus cereus* Group Bacteria with the PCR." *International Journal of Systematic Bacteriology* 44(1):99-105.
Henderson, I., et al. (1995) "Differentiation of *Bacillus anthracis* and other *'Bacillus cereus* group' bacteria using IS231-dervied sequences." *FEMS Microbiology Letters* 128:113-118.
Hutson, R.A., et al. (1993) "The development and assessment of DNA and oligonucleotide probes for the specific detection of *Bacillus anthracis." Journal of Applied Bacteriology* 75:463-472.
Jackson, P.J., et al. (1999) "Genetic comparison of *Bacillus anthracis* and its close relatives using amplified fragment length polymorphism and polymerase chain reaction analysis." *Journal of Applied Microbiology* 87:263-269.
Keim, P., et al. (1997) "Molecular Evolution and Diversity in *Bacillus anthracis* as Detected by Amplified Fragment Length Polymorphism Markers." *Journal of Bacteriology* 179(3):818-824.
Lane, D.J. (1991) "16S/23S rRNA sequencing." Ed. E. Stackenbrandt and M. Goodfellow, *Nucleic acid techniques in bacterial systematics*, John Wiley & Sons 115-176.
Longchamp, P. and Leighton, T. (1999) "Moleclar recognition specificty of *Bacillus anthracis* spore antibodies." *Journal of Applied Microbiology* 87:246-249.
Patra, G., et al. (1996) "DNA fingerprinting of *Bacillus anthracis* strains." *Salisbury Medical Bulletin, Special Supplement* No. 87:59.
Patra, G., et al. (1996) "Isolation of a specific chromosomic DNA sequence of *Bacillus anthracis* and its possible use in diagnosis." *FEMS Immunology and Medical Microbiology* 15:223-231.
Priest, F.G., et al. (1994) "Characterization of *Bacillus thuringiensis* and related bacteria by ribosomal RNA gene restriction fragment length polymorphisms." *Microbiology* 140:1015-1022.
Proudnikov, D., et al. (1998) "Immobilization of DNA in Polyacrylamide Gel for the Manufacture of DNA and DNA-Oligonucleotide Microchips." *Analytical Biochemistry* 259:34-41.
Ramisse, V., et al. (1996) "Identification and characterization of *Bacillus anthracis* by multiplex PCR analysis of sequences on plasmids pXO1 and pX02 and chromosomal DNA." *FEMS Microbiology Letters* 145:9-16.
Ryzhov, V., et al. (2000) "Rapid Characterization of Spores of *Bacillus cereus* Group Bacteria by Matrix-Assisted Laser Desorption-Ionization Time-of-Flight Mass Spectrometry." *Applied and Environmental Microbiology* 66(9):3828-3834.
Shangkuan, Y.-H., et al. "Comparison of PCR-RFLP, ribotyping and ERIC-PCR for typing *Bacillus anthracis* and *Bacillus cereus* strains." *Journal of Applied Microbiology* 89:452-462, Sep. 2000.
Stahl, D.A. and Amann, R. (2001) "Development and Application of Nucleic Acid Probes." Ed. E. Stackebrandt and M. Goodfellow, *Nucleic acid techniques in bacterial systematics*, John Wiley & Sons 205-248.
Strizhkov, B.N., et al. (2000) "PCR Amplification on a Microarray of Gel-Immobilized Oligonucleotides: Detection of Bacterial Toxin- and Drug-Resistant Genes and their Mutations." *BioTechniques* 29:844-857.
Wunschel, D., et al. (1994) "Discrimination Among the *B. cereus* Group, in Comparison to *B. subtilis*, by Structural Carbohydrate Profiles and Ribosomal RNA Spacer Region PCR." *Syste, Appl. Microbiol.* 17:625-635.
Yershov, G., et al. (1996) "DNA analysis and diagonstics on oligonucleotide microchips." *Proc. Nat'l. Acad. Sci. USA* 93:4913-4918.
Zlatanova, J. and Mirzabekov, A. (2001) "Gel-Immobilized Microarrays of Nucleic Acids and Proteins." *Methods in Molecular Biology* 170:17-38.

* cited by examiner

|  | ps21/ps22 | ps21/ps22 signal ratio | site 1559 in 23S rRNA | G/A ratio in site 1559 |
|---|---|---|---|---|
| B. anthracis Ames (Anthracis) | | 1.80 | G | - |
| B. mycoides ATCC10206 (Mycoides B) | | 1.50 | G | - |
| B. cereus T (Cereus B) | | 1.00 | R | 1.5 |
| B. thuringiensis 4Q281 (Thuringiensis B) | | 0.72 | R | 1 |
| B. cereus NCTC9620 (Cereus B) | | 0.64 | R | 0.3 |
| B. thuringiensis B8 (Cereu A) | | 0.45 | A | - |

Fig. 5(A)

| Subgroup | | ps21/ps22 | ps21/ps22 signal ratio | ps23/ps24 | ps23/ps24 signal ratio | ps18/ps17 |
|---|---|---|---|---|---|---|
| Cereus A | B. cereus HER 1414 | ☐ ◼ | 0,7 | ☐ ☐ | 0,7 | ☐ ☐ |
| | B. thuringiensis B8 | ☐ ☐ | 0,4 | ☐ ◼ | 0,4 | ☐ |
| Anthracis | B. anthracis Sterne | ◼ ☐ | 2,2 | ◼ ☐ | 1,7 | ☐ |

B.cereus NCTC9620

1 : 3 ps17  ps18

Bacterial RNA Mixture (2 : 3)
B.cereus NCTC9620 & B.anthracis AMES

3 : 2 ps17  ps18

B.anthracis AMES

8 : 1 ps17  ps18

B

B.thuringiensis 4Q281 ps5  ps6    1 : 5
ps7  ps8    1 : 4
ps17 ps18   1 : 4

Bacterial RNA Mixture (10 : 1)
B.thuringiensis 4Q281 & B.thuringiensis B8 ps5  ps6    1 : 2
ps7  ps8    1 : 3
ps17 ps18   2 : 5

B.thuringiensis B8
(B.anthracis mimic)

| Microorganism | Cereus group | Subtilis group | Signal ratio |
|---|---|---|---|
| B.anthracis AMES | ◻ | | 9.5 |
| B.cereus T | ■ | | 8.3 |
| B.mycoides ATCC6462m | ◻ | | 7.8 |
| B.thuringiensis 4Q281 | ◻ | | 8.1 |
| B.subtilis B-459 | | ◻ | 0.4 | ps 25   ps 26

| 23F1 not Myc A, B | 23F2 Myc A, B | #54 not Myc B | SB25 Myc B | B1 Antr, Cer A, B | B2 Thur B, Myc B | SB22 not Antr, Cer A, Myc B | SB23 Antr, Cer A Myc B | A1 not Thur B, Myc A |
|---|---|---|---|---|---|---|---|---|
| 23F5 not Myc A | 23F6 Myc A | SB10 not Myc B | SB11 Myc B | B7 Antr, Cer A, B | B8 Thur B, Myc B | B11 Antr | B12 Cer A | A2 Thur B, Myc A |
| 23F7 not Myc A | 23F8 Myc A | | E7 Hybrid Marker | C5 Antr, Cer A, B | C6 Thur B, Myc B | C9 Antr | C10 Cer A | A5 not Thur B, Myc A |
| 16A1 not Myc A | 16A2 Myc A | A7 not Myc B | A8 Myc B | C7 Antr, Cer A, B | C8 Thur B, Myc B | | E7 Hybrid Marker | A6 Thur B, Myc A |
| 16A3 not Myc A | 16A4 Myc A | 23F3 not Myc B | 23F4 Myc B | A3 Antr, Cer A, B | A4 Thur B, Myc B | C11 Antr | C12 Cer A | A9 not Thur B, Myc B |
| 16A5 not Myc A | 16A6 Myc A | E7 Hybrid Marker | | | | SB12 B med, not Thur A, B | D4 Thur A, B | A10 Thur B, Myc B |
| 16A7 not Myc A | 16A8 Myc A | SB23 Antr, Cer A, Myc B | SB22 not Antr, Cer A Myc B | 23F13 Antr | 23F14 Cer A | SB15 not Thur B | SB16 Thur B | A11 not Thur B, Myc B |
| 16A9 not Myc A | 16A10 Myc A | D1 Antr, Cer A, Myc B | D2A not Antr, Cer A, Myc B | 23F15 Antr | 23F16 Cer A | SB4 not Thur B | SB4A Thur B | A12 Thur B, Myc B |

[Chip ## 776-790]

FIG. 8

DISCRIMINATION OF BACILLUS ANTHRACIS FROM CLOSELY RELATED MICROORGANISMS BY ANALYSIS OF 16S AND 23S RRNA WITH OLIGONUCLEOTIDE MICROCHIPS

This application claims priority to co-pending U.S. Ser. No. 60/336,319 filed Nov. 2, 2001 and is a continuation-in-part of U.S. Ser. No. 10/212,476 filed Aug. 5, 2002 which is a divisional of U.S. Ser. No. 09/261,115 filed Mar. 3, 1999, now U.S. Pat. No. 6,458,584, which is a continuation-in-part of U.S. Ser. No. 08/780,026 filed on Dec. 23, 1996, now abandoned.

The United States Government has rights in this invention under Contract No. W-31-109-ENG-38 between the U.S. Department of Energy and the University of Chicago representing Argonne National Laboratory.

FIELD OF THE INVENTION

Methods and compositions are provided for the detection of Bacillus anthracis from closely related microorganisms of the B. cereus group, and to distinguish and classify the B. cereus group. A customized, analytical oligonucleotide microchip incorporating 16S and 23S rRNA-targeted nucleic acid probes, is used for the detection of B. anthracis and discrimination.

BACKGROUND

Bacillus anthracis, the causative agent of the highly infectious disease anthrax, belongs to the Bacillus cereus group, which also contains six other closely related species: Bacillus cereus, Bacillus thuringiensis, Bacillus mycoides, Bacillus pseudomycoides, Bacillus weihenstephanensis and Bacillus medusa. A variety of methods have been reported for the selective identification of B. anthracis. These include direct testing of bacterial DNA with specific probes, PCR amplification followed by an in-tube assay, PCR with subsequent electrophoretic analysis of length variation among ribosomal operons, ribotyping, amplified fragment length polymorphisms, methods of analysis using plasmid and chromosomal sequences, PCR-ELISA, on chip PCR amplification of anthrax toxin genes, detection of unique polysaccharides and other biomarkers on B. anthracis cell surface with mass spectrometry, immunological recognition of spores and vegetative cells and determination of phenotypic characteristics. The main goal of the various methods is rapid and inexpensive detection of this extremely pathogenic microorganism so that containment, destruction of the pathogens and treatment are facilitated.

Hybridization analysis of 16S rRNA is a method of microbial identification. The 16S rRNA molecule is suitable for use as a target for microbial identification and detection. Although conserved in sequence overall, the 16S rRNAs actually exhibit significant variation in some regions. These differences in 16S rRNA sequences provide the basis for the design of nucleic acid probes of varying specificity, ranging from probes targeting all living organisms, to group-specific and species-specific probes. Another advantage of using the rRNAs as a target is the fact that these molecules are naturally amplified within the cell. In general, rRNA represents about 80% of total nucleic acids in microbial cells, and thus is present in many hundreds and thousands of copies per cell. This natural amplification allows for direct detection of rRNA sequences without the need for intermediate amplification via PCR.

The main limitations of current hybridization techniques in general are that they are time consuming and limited in terms of the number of probes which can be analyzed simultaneously. Oligonucleotide microchip technology is a rapid and high throughput platform for nucleic acid hybridization reactions. Moreover, a universal mini-column (syringe-operated silica mini-column) for nucleic acid isolation, fractionation, fragmentation, fluorescent labeling, and purification, as well as an inexpensive, portable fluorescent analyzer for hybridization imaging was reported. Using the prototype mini-column, oligonucleotide microchip and portable imager, hybridization patterns from both microbial and human cells were detected in less than 60 minutes.

Current detection techniques for B. anthracis identification such as PCR, electrophoretic analysis, PCR-ELISA, and mass-spectrometry require a considerable amount of time, are expensive, and are generally limited by the number of probes analyzed. Moreover, some of these detection techniques are incapable of discriminating closely related isolates, especially isolates that are differentiated by as little as a single base change in DNA or RNA. In addition to being expensive and time-consuming, many of these methods are not portable. The present invention is designed to address many of the problems mentioned above.

SUMMARY OF THE INVENTION

The present invention relates to methods and compositions for using nucleotide sequence variations of 16S and 23S rRNA within the B. cereus group to discriminate B. anthracis from closely related microorganisms. The existence of sequence variability within the B. cereus group was useful to consistently determine the identity of B. cereus isolates including B. anthracis. To accomplish this goal a set of 16S and 23S rRNA targeted oligonucleotide probes was designed to discriminate among the seven subgroups within B. cereus, and in particular to discriminate B. anthracis from other members in the B. cereus group. The sequences for these probes were selected so that they are complementary to target rRNA sequences. These probes were incorporated into an oligonucleotide microchip. Feasibility of discrimination of single base differences in rRNA was demonstrated with this microchip during analysis of B. cereus group isolates from both single and mixed cultures. Rapid, selective identification of B. anthracis from a mixture of closely related microorganisms has valuable application in diagnosis and epidemiological monitoring.

A method for detecting a particular isolate of B. cereus subgroups, including B. anthracis in a sample, includes the steps of:

(a) Placing on a microchip oligonucleotide probes targeted to rRNA sequences, that discriminate the B. cereus subgroups.

(b) Providing conditions for hybridization of the probes with rRNA from the sample.

(c) Analyzing hybridization signals in the microchip from which the particular isolate is detected.

The oligonucleotide probes are directed to 16S rRNA or 23S rRNA.

The probes may be labeled, e.g. with a fluorescent dye.

A microarray with oligonucleotide probes selected from a group of sequences designated:

| Oligonucleotide Name | 5' to 3' Sequence |
|---|---|
| ps1 | GAGCGAATGGATTAAGAGCT (SEQ ID NO: 1) |
| ps2 | GAGCGAATGGATTgAGAGCT (SEQ ID NO: 2) |
| ps3 | AGCTTGCTCTTATGAAGTTA (SEQ ID NO: 3) |
| ps4 | AGCTTGCTCTcAaGAAGTTA (SEQ ID NO: 4) |
| ps5 | TGCTCTTATGAAGTTAGCGG (SEQ ID NO: 5) |
| ps6 | TGCTCTcAaGAAGTTAGCGG (SEQ ID NO: 6) |
| ps7 | CATTTTGAACCGCATGGTTC (SEQ ID NO: 7) |
| ps8 | CATTTTGAACtGCATGGTTC (SEQ ID NO: 8) |
| ps9 | CATTTTGAACCGCATGGTTC (SEQ ID NO: 9) |
| ps10 | CATTTTGcACCGCATGGTgC (SEQ ID NO: 10) |
| ps11 | AACCGCATGGTTCGAAATTG (SEQ ID NO: 11) |
| ps12 | CACCGCATGGTgCGAAATTc (SEQ ID NO: 12) |
| ps13 | ATGGTTCGAAATTGAAAGGC (SEQ ID NO: 13) |
| ps14 | ATGGTgCGAAATTcAAAGGC (SEQ ID NO: 14) |
| ps15 | GAAATTGAAAGGCGGCTTCG (SEQ ID NO: 15) |
| ps16 | GAAATTcAAAGGCGGCTTCG (SEQ ID NO: 16) |
| ps17 | CATCCTCTGACAACCCTAGA (SEQ ID NO: 17) |
| ps18 | CATCCTCTGAaAACCCTAGA (SEQ ID NO: 18) |
| ps19 | GCTTCTCCTTCGGGAGCAGA (SEQ ID NO: 19) |
| ps20 | GCTTCcCCTTCGGGgGCAGA (SEQ ID NO: 20) |
| ps21 | TTATCGTGAAGGCTGAGCTG (SEQ ID NO: 21) |
| ps22 | TTATCGTaAAGGCTGAGCTG (SEQ ID NO: 22) |
| ps23 | TGATACC-AATGGTATCAGTG (SEQ ID NO: 23) |
| ps24 | TGATACCgAATGGTATCAGTG (SEQ ID NO: 24) |

Lower case letters refer to positions of mismatches (see FIGS. 1 and 2).

The oligonucleotides may be arranged in pairs in specific patterns, for example, a customized microchip wherein I, II, III and IV are columns and A, B, C, D, E, and F are rows in the microchip design as follows:

|   | I | II | III | IV |
|---|---|---|---|---|
| A | ps19 | ps20 | ps7 | ps8 |
| B | ps15 | ps16 | ps3 | ps4 |
| C | ps9 | ps10 | ps5 | ps6 |
| D | ps13 | ps14 | ps1 | ps2 |
| E | ps11 | ps12 | — | — |
| F | — | — | ps17 | ps18 |

A diagnostic kit to detect *B. anthracis* target rRNA in a sample, includes in separate compartments:

(a) A microchip that comprises at least one oligonucleotide probe to distinguish variations among *B. cereus* group isolates.

(b) Means for detecting hybridization between the probes and a target rRNA by which *B. anthracis* is detected.

A customized microchip is shown in FIG. 8, wherein oligonucleotides are selected from those listed in Table 5.

A method for taxonomically classifying *B. cereus* group includes the steps of:

(a) developing strain- and subgroup-specific signature profiles of 16S and 23S rRNA sequences for *B. cereus* group isolates; and (b) using the signature profiles to construct phylogenetic trees in order to classify the various *B. cereus* group isolates.

An isolate is a particular genetic variant of a species. If one isolate is known, then it defines the species. However, there can be many different isolates of one species, isolated for example, from different patients or different parts of the world.

Sample includes biological samples such as blood, skin, bodily fluids and tissues and environmental samples such as air, food, water and soil.

BRIEF DESCRIPTION OF THE FIGURES

FIG. 4 illustrates the identification of reference microorganisms and subgroups to which they belong in the *B. cereus* group with a 16S rRNA oligonucleotide microchip. Total RNA from reference microorganisms was isolated, fluorescently labeled with Texas Red, and hybridized with a microchip bearing 20 bases of oligonucleotides as described in MATERIALS AND METHODS. Positions of the probes and targeted subgroups (in rectangles) are indicated in the upper left corner. Members of the targeted subgroup form perfect matches with probes indicated with arrows. For probe abbreviations see FIG. 1.

FIG. 5 illustrates the identification of single-base polymorphisms (A) and differentiation of *Cereus* A subgroup bacteria (*B. thuringiensis* B8 and *B. cereus* 1414) from organisms of *Anthracis* subgroup (*B. anthracis* Ames) (B), using hybridization of fluorescently labeled total RNA from *B. cereus* group bacteria to probes targeting the 23S rRNA. R=G, or A. Probe signal ratio was calculated as the average from 2-4 experiments.

FIG. 6 illustrates the identification of 16S rRNA of (A) *B. anthracis* Ames in a mixture (3:2) with *B. cereus* NCTC9620 16S rRNA and (B) *B. thuringiensis* B8 (*B. anthracis* mimic) 16S rRNA mixed with *B. thuringiensis* 4Q281 16S rRNA in the ratio 1:10. Total RNA of the studied bacteria was isolated, fluorescently labeled as described in MATERIALS AND METHODS, mixed in the above mentioned proportions, and hybridized with oligonucleotide microchip. For probe abbreviations shown on the left and right sides of panels, see FIG. 1. Bold numbers indicate the ratio of integrated fluorescent signals after hybridization.

FIG. 7 illustrates the identification of microbial groups using a 16S rRNA oligonucleotide microchip. A microchip containing oligonucleotides ps25 and ps26 targeting the *B.* cereus group (5'-CGGTCTTGCAGCTCTTTGTA-3') (SEQ ID NO: 25) and the *B. subtilis* group (5'-ATTCCAGCT-TCACGCAGTC-3') (SEQ ID NO: 26), respectively. Microchips were hybridized with fluorescently labeled total RNA of the corresponding microorganisms. Ratios of integrated fluorescent signals are shown in the far right column.

Figure 1:
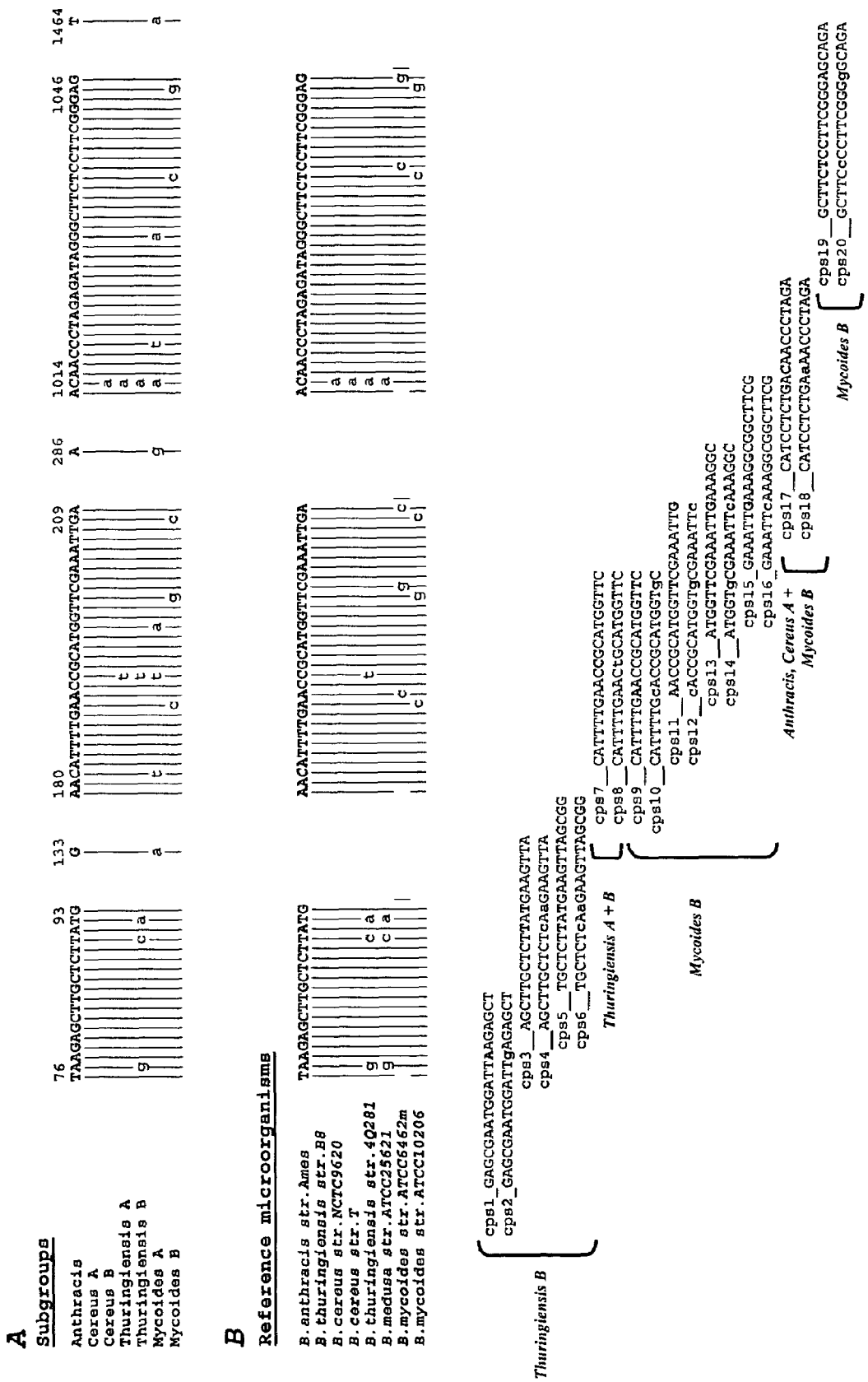
FIG. 1 illustrates the positions of subgroup-specific sequence differences in the 16S rRNA gene of *B. cereus* subgroups (A) (SEQ ID NOS 122-142) and reference microorganisms used for microchip testing (B) (SEQ ID NOS 143-166). The sequence of *B. anthracis* Ames ANR was used as the consensus sequence. Sequences which are complementary to the probes on a microchip and their locations on the 16S rRNA are also shown (bold letters denote target nucleotides). The names of the probes (example, ps1) are shown to the left of each of the sequences (SEQ ID NOS 1-20). The target species for each of the probes are indicated to the left of the parenthesis.

FIG. 8 is a map of a microchip with molecules in positions designated by squares, that have sequences in accord with those in Table 5.

DETAILED DESCRIPTION OF THE INVENTION

Aspects of the invention include:
1. microchips designed to detect a particular isolate of *B. cereus* subgroup, including *B. anthracis* based on sequence variations in the 16S and 23S rRNAs; the sequence variations are chosen so that hybridization signals discriminate a particular isolate from other closely related organisms; using at least one mismatched sequence; and
2. methods for improved taxonomic classification and detection of *B. cereus* group isolates based on individual strain variations of 16S and 23S rRNA sequences.

The microchips of the present invention overcome some of the limitations of current hybridization techniques to detect *B. anthracis*. The microchip-based detection of variations in rRNA sequences is rapid, reliable, and capable of high throughput. Additionally, small sequence variations such as single nucleotide polymorphisms (SNPs) among closely related isolates can be effectively discriminated with the microchip disclosed in the present invention. Because rRNA-based hybridization does not require PCR amplification, a direct and efficient method of detection is possible with microchips. Hybridization signals can be analyzed by an inexpensive fluorescent analyzer, which is also portable. This portability coupled with the ease of detecting *B. anthracis*, a highly infectious agent render the current invention a valuable tool for public health safety measures.

The present invention also discloses variations of 16S and 23S rRNA sequences among *B. cereus* isolates. These sequence variations are essential to correctly classify closely related microorganisms. Thorough analysis of 16S and 23S rRNA sequence variations in *B. cereus* group isolates revealed certain subgroup- and strain-specific signatures that aid in the grouping of closely related isolates. Correct classification of these isolates is important to identify the close relationships and to develop better analytical methods to discriminate among the isolates. For example, appropriate clustering of subgroup-specific sequence variants of the present invention provides the basis for the design of a number of diagnostic oligonucleotide probes to discriminate each of the subgroups within the *B. cereus* group.

Diagnostic kits to discriminate *B. anthracis* from closely related microorganisms include:
(a) At least one microchip that includes at least one oligonucleotide probe that is discriminating, usually distinguishing among related organisms by at least one mismatch between target rRNA sequences. Suitable probes are those in Table 5;
(b) Means for detecting hybridization signals between labeled RNA and oligonucleotides on the microchip.

Means for detecting hybridization signals include a fluorescence microscope equipped with a CCD camera or a laser scanner. Reagents for isolating total RNA include nucleic-acid spin columns (Bavykin et al., 2001) and GITC-based RNA extraction reagents. Fluorescent dyes such as Liss-Rhod (Lissamine™ rhodamine B ethylenediamine; Cat # L2424PO Molecular Probes Eugene, Oreg.) and cyanine dyes (Glen Research Inc., Sterling, Va.) can be used to label rRNA molecules isolated from microorganisms.

Customized oligonucleotide microchips are aspects of the invention. The microchip includes a matrix support, which can be made from elements such as glass, and polyacrylamide. An embodiment of a microchip is:
(a) ten pairs of oligonucleotide probes that target 16S rRNA sequences and two pairs of oligonucleotide probes targeting 23S rRNA sequences; the oligonucleotides are synthesized to include a 5'-amino-modifier;
(b) microchips containing polyacrylamide gel pads with aldehyde groups; and
(c) six nl of individual amino-oligonucleotide solutions in each gel pad element.

An embodiment of a customized microchip includes an array wherein oligonucleotides are arranged in a specific pattern as in FIG. 8 and sequences of the oligonucleotides are selected from Table 5. Another embodiment of a customized microchip is an array wherein oligonucleotide probes are immobilized in a specific pattern as in FIG. 4 and the probe sequences are selected from FIG. 1B (ps1 through ps20). Using these customized microchips, *B. anthracis* can be discriminated from other closely related isolates.

Identification of Subgroups and Strains in *B. cereus* Group with rRNA Probes

Figure 3A:
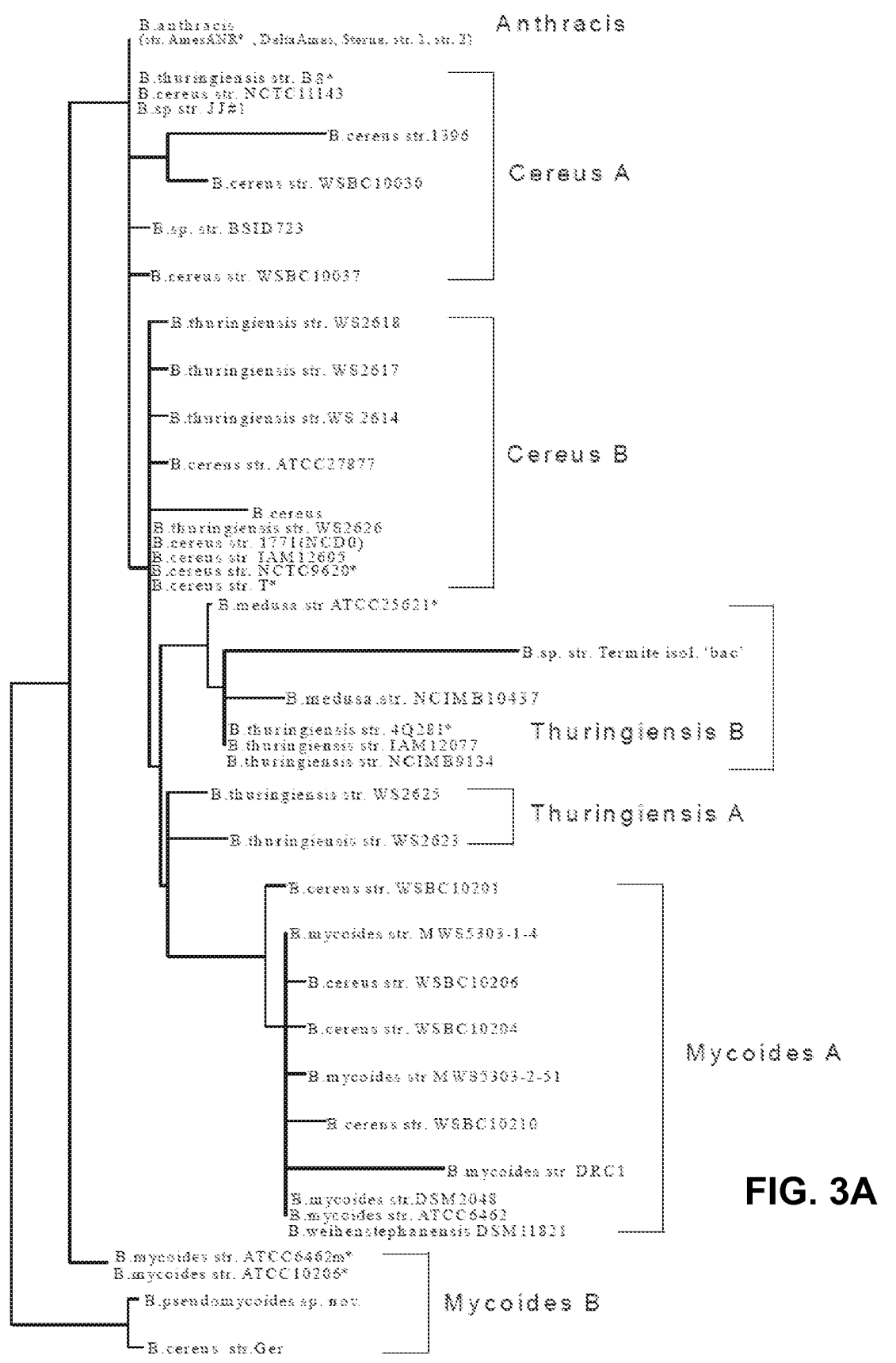
Figure 3B:
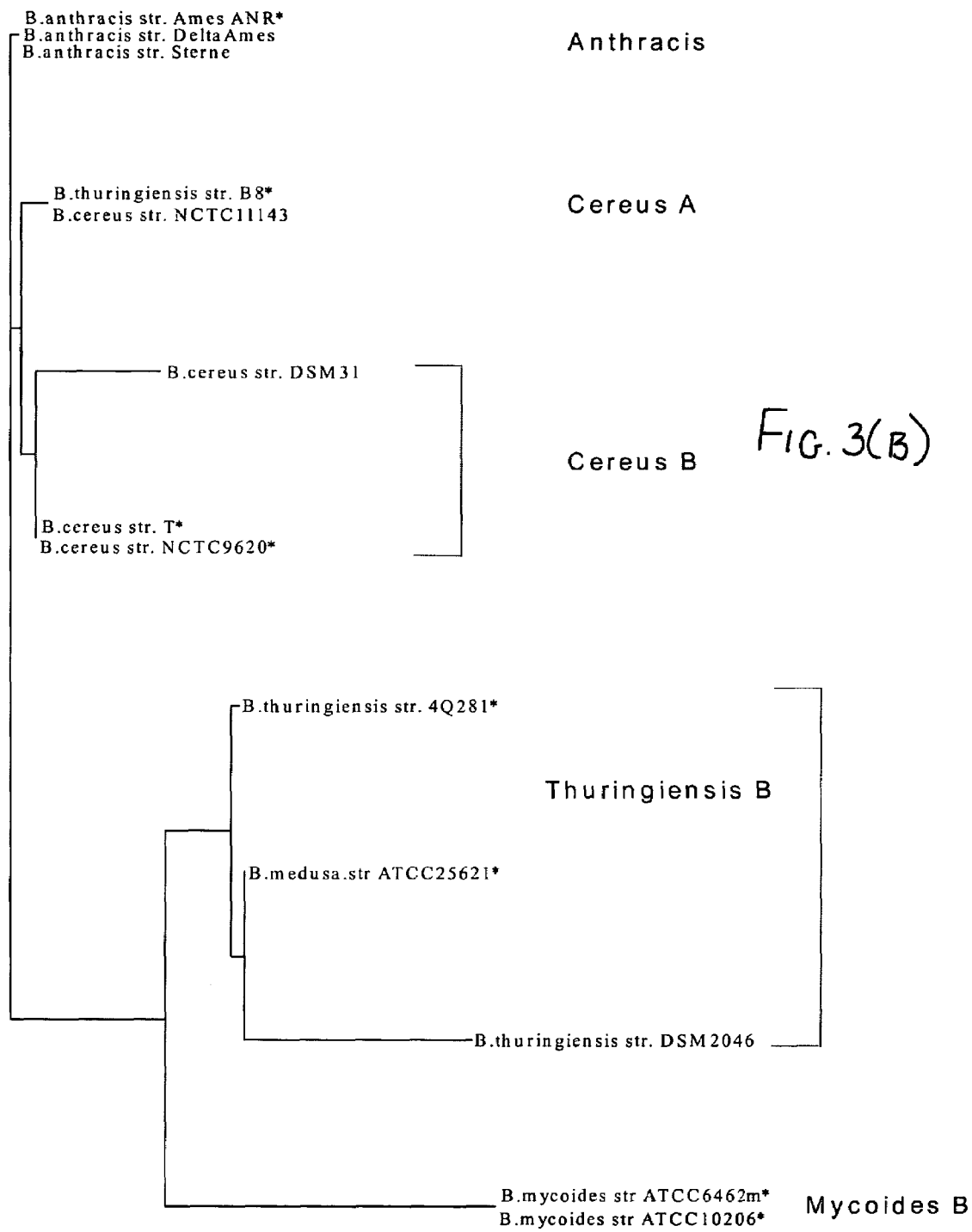
FIG. 3 illustrates the phylogenetic trees of (A) 16S and (B) 23S rRNA genes of bacteria in *B. cereus* group. Analysis was performed done using the multiple sequence alignment computer program "Clustalx" (ftp://ftp-igbmc.u-strausbg.fr/pub/clustalx/), and "Clustlaw" (http://www.ebi.ac.uk/clust-law). Asterisks indicate the reference microorganisms which were used.

Based on 16S rRNA sequence analysis, the *B. cereus* group was divided into seven subgroups (*Anthracis*, *Cereus* A and B, *Thuringiensis* A and B and *Mycoides* A and B) each containing microorganisms with similar 16S rRNA gene sequences (FIG. 3A and Table 2). The strains within each subgroup contained all of the sequence variants specific for that subgroup. The 23S rRNA sequencing confirmed these subgroup classifications (FIG. 3B and Table 3). Some of the subgroup-specific signatures, indicated in Table 2, have already been reported for identification of certain *Bacillus* strains. For example, *B. thuringiensis* was differentiated from *B. cereus* based on a sequence difference in region 77-92. However, only isolates from subgroup *Thuringiensis* B, and not isolates from subgroup *Thuringiensis* A (FIG. 1 and Table 2), could be differentiated based on this sequence difference. Psychrotolerant strains of *B. cereus* or *B. mycoides* have been identified based on differences in regions 182-197 and 1019-1030 of their 16S rRNA sequences, but these signatures describe organisms from subgroup *mycoides* A only, and not isolates from subgroup *mycoides* B (FIG. 1 and Table 2). Therefore, systematic analysis of all *B. cereus* group microorganisms had not been done.

A set of 16S rRNA targeted oligonucleotide probes (FIG. 1) is constructed of 3-D gel pads. These probes were immobilized within a oligonucleotide microchip. This microchip enabled differentiation of *B. anthracis* Ames (subgroup *Anthracis*) and *B. thuringiensis* B8 (subgroup *Cereus* A) from six reference strains of closely related organisms (*B. cereus* T, *B. thuringiensis* 4Q281, *B. medusa* ATCC25621, *B. mycoides* ATCC 6462m, *B. mycoides* ATCC 10206. *B. cereus* 9620) representing three different subgroups, *Cereus* B, *Thuringiensis* B and *Mycoides* B, respectively. An embodiment of the present invention is a customized microchip capable of identifying organisms of subgroups *Thuringiensis* A. Comparison of hybridization signals from probe pairs ps1/ps2, ps3/ps4 and ps5/ps6 with signals from pair ps7/ps8 on the microchip (FIG. 1) demonstrated that *B. thuringiensis* str. 4W1, 4T1, 4F1 and 4D1 belong to subgroup *Thuringiensis* A, whereas *B. thuringiensis* str. 4Q1, 4Q2, 4A1 and 4A7 belong to subgroup *Thuringiensis* B.

Because the RNA sequences of bacteria from the *Mycoides* A subgroup became available only recently, specific probes were not selected for those microorganisms. However, the microchip in the configuration disclosed herein has the capability to recognize organisms of *Mycoides* A subgroup. Results of microchip hybridization is similar with subgroup *Thuringiensis* A organisms, but signals from pairs ps7/ps8, ps9/ps10, and ps11/ps12 (FIG. 1) are considerably decreased in comparison with that one for *Thuringiensis* A, because of the forming of two additional mismatches for ps7/ps8 and ps9/ps10, and one additional mismatch in the middle of the probes, ps11/ps12. Signals from the probes ps13/ps14 and ps17/18 may be also decreased because of the presence of one additional mismatch in the terminal end of these probes. However, discrimination is easily achieved using regions 120-145, 166-188, 1015-1035 on 16S rRNA and region 366-390 on the 23S rRNA genes as probe targets. Probes for these regions have also been selected and applied on the second generation of microchips for identification f *B. cereus* group microorganisms (FIG. 8, Table 5).

Another embodiment of the present invention is a method for differentiating microbial strains that differ by only one base in their 16S rRNA molecule both separately (FIG. 4) and in mixtures (FIG. 6). Thus it is possible to identify all strains within the *B. cereus* group that differ by as little as a single nucleotide change in their rRNA sequences. Based on 16S rRNA sequence differences (Table 2), the microchip also serves to differentiate isolates of subgroup *Anthracis* and subgroup *Cereus* A from all other thirty-two studied strains of bacteria in the *B. cereus* group and to identify which subgroup (Table 2) each microorganism belongs (FIG. 4), even in a 1:10 mixture (FIG. 6B).

Another embodiment of the present invention is to be able to identify *B. cereus* isolates by the sequence variations in their 23S rRNA. The 23S rRNA gene was sequenced for a selected set of reference strains of the *B. cereus* group. Isolates from subgroup *Cereus* A, which has the same 16S rRNA sequence as *B. anthracis* Ames (FIG. 1 and Table 2), have three changes in the 23S rRNA sequence in comparison with *B. anthracis* Ames (FIG. 2 and Table 3). *B. thuringiensis* B8 and *B. cereus* HER1414 were used to demonstrate that these sites may be utilized for discrimination between subgroups *Anthracis* and *Cereus* A (FIG. 5).

Study of site 1559 on the 23S rRNA, where a number of strains revealed single-base changes, demonstrated that the microchip also enabled a single-base polymorphism to be recognized (FIG. 5A).

Previous work has shown that 16S rRNA sequences for *B. anthracis* Sterne, *B. cereus* NCDO1771 and *B. cereus* NCTC 11143 have 99.9-100% similarity (Table 1). However, all three organisms, as well as other isolates that belong to *Cereus* A subgroup, are differentiated using subgroup-specific signatures, or strain-specific variations and a combination of 16S and 23S rRNA-targeted probes (Tables 2 and 3). False negative identifications, are not expected i.e. will effectively recognize the presence of *B. anthracis*. Some false positive identifications occurred, i.e. mistaken identification of *B. anthracis* strains that list their virulence as *B. anthracis*. However, for the identification of a species, which produces a toxin as hazardous as anthrax, a small number of false positive reactions is preferable to any false negative signals.

Therefore, the microchips (FIG. 4 and FIG. 8) is capable of discriminating all seven subgroups of the *B. cereus* group, and thus microchip analysis of ribosomal RNA serves as a powerful tool for identification of *B. cereus* group bacteria.

Taxonomy of the *B. cereus* Group

The results of analysis of 16S and 23S rRNA sequences show some disagreement with the current taxonomic classification of species within the *B. cereus* group. Traditionally, classification of microorganisms in the *B. cereus* group has been based on morphological, physiological, and immunological data. However, some data suggests that there may be some difficulties with these classification schemes. *B. thuringiensis* has been traditionally distinguished from *B. cereus* by the production of a parasporal crystal of a protein that is toxic for Lepidoptera, Diptera and Coleoptera larvae. The capacity to form crystals is plasmid-encoded, however, the plasmid may be lost by laboratory culturing. Moreover, authentic cultures of *B. cereus* and *B. anthracis* can acquire the ability to produce crystals as a result of growing in mixed culture with *B. thuringiensis*. Thus, the discrimination of *B. cereus* from *B. thuringiensis* is a difficult task by any method, and the fact that they have grouped together in the present analysis is not surprising. At the same time, some *B. thuringiensis* strains may be moved (reassigned) after resequencing their 16S rRNA from subgroup *Cereus* B to subgroup *Thuringiensis* B, which differ from each other by only one subgroup-specific signature C/T(192) (Table 2).

Sporadic loss of the ability to form rhizoid colonies has been observed in several strains of *B. mycoides*, indicating an instability of morphology in this species. DNA relatedness studies have indicated that the species *B. mycoides* actually consists of two genetically distinct groups. The fact that methods and compositions of the present invention place *B. mycoides* strains into two subgroups, *Mycoides* A and *Mycoides* B, supports this finding. Bacterial strains can also undergo physiological changes after the loss or acquisition of plasmids coding for toxins, sporulation, or antibiotic resistance.

According to the present classification scheme (Table 2), four representatives of psychrotolerant strains of *B. cereus* (WSBC10201, WSBC10204, WSBC10206 and WSBC10210), which were recently named as the new species *B. weihenstephanensis*, fall under subgroup *Mycoides* A. This finding suggests that species *B. weihenstephanensis* may be one of the *B. mycoides* strains that belongs to the subgroup *Mycoides* A. This suggestion is confirmed by the high degree of similarity of genomic DNA sequences (85-88%) between *B. cereus* strains WSBC10201, WSBC10204, and WSBC10206 and *B. mycoides* DSM2048, which is also located in subgroup *Mycoides* A. In addition, based on the ability to grow at low temperature, *B. mycoides* is the most closely related species to *B. weihenstephanensis* in the *B. cereus* group.

EXAMPLES

Example 1

Sequencing of 16S and 23S rRNA Genes of *B. cereus* Group Microorganisms

Twelve 16S rRNA and ten 23S rRNA genes were sequenced (Tables 2, 3). There are published sequences available for two of the strains that were sequenced, *B. medusa* NCIMB 10437 (ATCC 25621) and *B. anthracis* Sterne. There were some discrepancies between the present sequences and the previously published sequences. The published 16S rRNA sequences of *B. anthracis* Sterne (GenBank AC: X55059) and *B. medusa* NCIMB 10437 (GenBank AC X60628) have a deletion of C (942) in comparison with other strains of *B. anthracis* and *B. medusa* that were sequenced later (Table 2). This deletion was found neither in the present resequencing of *B. anthracis* Sterne (GenBank AC: AF176321) and *B. medusa* ATCC25621 (GenBank AC AF155958), nor in the present and in TIGR sequencing of *B. anthracis* Ames (GenBank AC:AF267734 and website http://www.tigr.org, respectively). It is likely that the reported deletion was a compression artifact of sequencing of the GC-rich region, i.e. -GGGGCCG- instead of -GGGGCCCG-. The same compression artifact may also have compromised the 16S rRNA sequences of *B. cereus* NCDO 1771, *B. cereus* NCTC 11143, *B. mycoides* DSM 2048 and *B. thuringiensis* NCIMB 9134 (GenBank AC:X55060 to X55063).

In addition, resequencing of the 16S rRNA gene for *B. medusa* ATCC 25621, did not reveal the C to T transition at position 192 (presence of T instead of C found in *B. anthracis*), or the A to G transversion at position 1383 previously reported for *B. medusa* NCIMB 10437 16S rRNA (Table 2).

Differences were also found in the previously published 23S rRNA sequence of *B. anthracis* Sterne (GenBank AC: S43426) and the present resequencing of this strain (GenBank AC: AT267877). The differences found were the following: T instead of C in position 491, deletion of CG(1413, 1414), and T instead of C in position 2651. These changes were not found in any other 23S rRNA sequence in *B. cereus* group, including *B. anthracis* Ames and *B. anthracis* DeltaAmes (Table 3). Therefore, it is likely that these differences in *B. anthracis* Sterne and also the same differences in *B. cereus* 11143 (GenBank AC X64646) are due to errors in the previously reported sequence.

Example 2

Comparison of 16S and 23S rRNA Sequences in the *B. cereus* Group

The present analysis indicated that in terms of known 16S and 23S rRNA sequences, *B. anthracis* was the most homogeneous species within the *B. cereus* group. This finding confirms PCR fingerprinting studies that demonstrated almost complete homogeneity of *B. anthracis* bulk DNA. In this work no reliably established variation in the 16S or 23S rRNA sequences was observed within any of the five *B. anthracis* strains characterized (Tables 2 and 3, FIGS. 1 and 2). Because of this homogeneity, and because *B. anthracis* is a target organism for the present invention, the *B. anthracis* 16S and 23S rRNA sequences were used as a reference for reporting differences among closely related bacteria within the *B. cereus* group (FIGS. 1 and 2, Tables 2 and 3).

The present analysis of 16S rRNA sequences for the other *B. cereus* group organisms identified six characteristic regions which contained the majority of the sequence differences among members of the groups: position(s) 77-92, 133, 182-208, 286, 1015-1045 and 1464 (FIG. 1 and Table 2). Because sequence variation in these regions can be used to divide the *B. cereus* group organisms into several large subgroups, the differences located within these regions were termed subgroup-specific signatures. Eighty percent of the strains of *B. cereus, B. thuringiensis, B. medusa, B. mycoides, B. pseudomycoides* and *B. weihenstephanensis* (32 of 40 sequences) analyzed contained some subgroup-specific signatures (Table 2) in their 16S rRNA sequences. The most common were C/A (1015) and C/T (192). In addition, a number of other differences were observed, which were termed strain-specific signatures (Table 2). These strain-specific signatures were unique to each strain and were located randomly along the 16S rRNA molecule, i.e., they did occur within the same sites as the subgroup-specific alterations. *B. anthracis* differed from 37 of the 40 other organisms within the *B. cereus* group by at least one sequence difference in the 16S rRNA.

Figure 2:
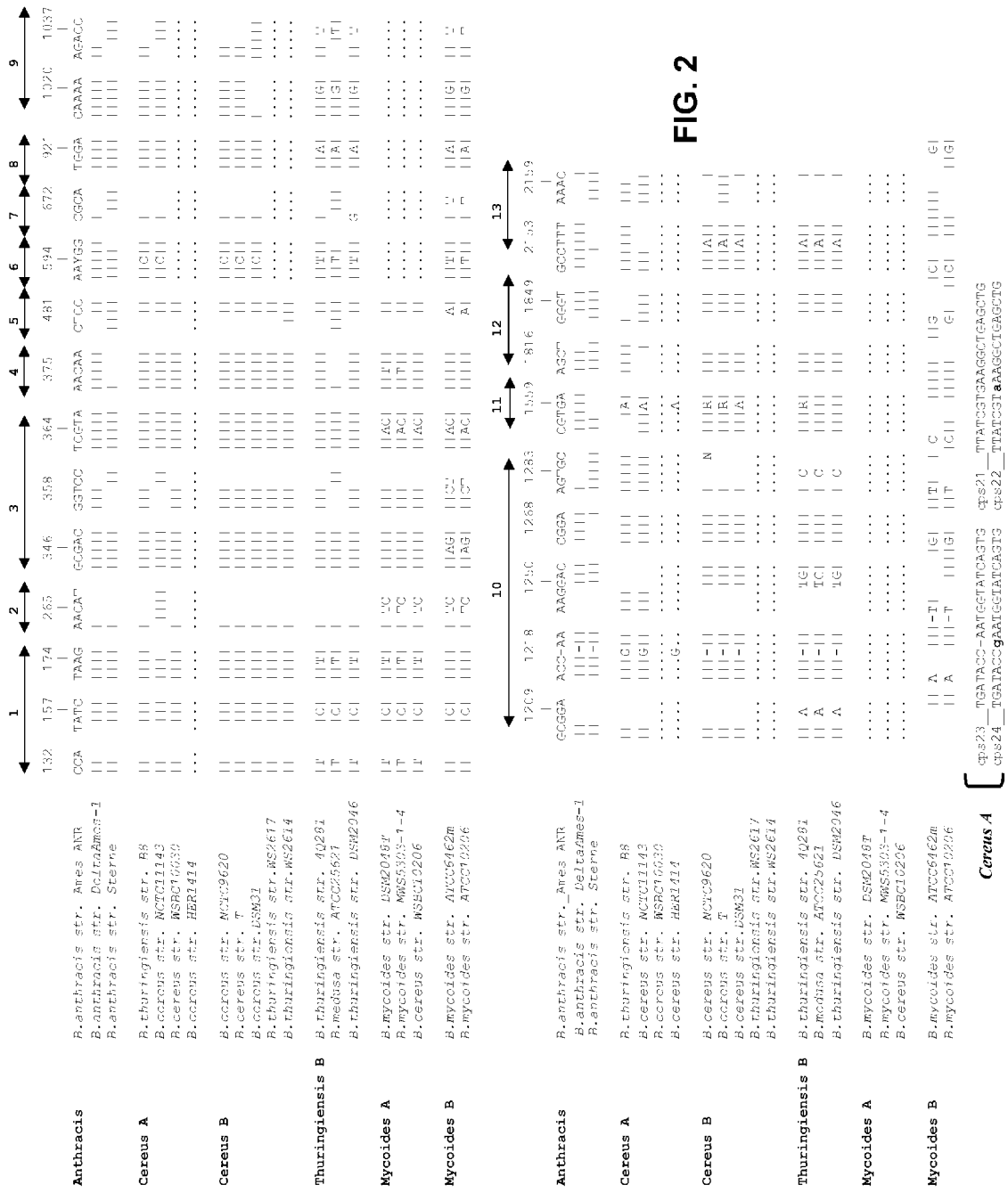
FIG. 2 illustrates the positions of subgroup-specific sequence differences in the 23S rRNA. The sequence of *B. anthracis* Ames ANR was used as the consensus sequence. Arrows indicate regions containing subgroup-specific signatures. Sequences complementary to the probes and their locations on the 23S rRNA are also shown (bold letters denote target nucleotides). The names of the probes (example, ps21) are shown to the left of the sequences (SEQ ID NOS 21-24). R=G, or A; Y=T, or C.

Analysis of the 23S rRNA sequences for the *B. cereus* group organisms revealed thirteen regions within which the majority of the sequence variation occurred (FIG. 2 and Table 3). The differences within these regions are analogous to the subgroup-specific signatures found in the 16S rRNA.

However, due to the limited number of 23S rRNA sequences in the GenBank database, it may be that not all of these differences are subgroup specific. Some of the regions, which appear to contain subgroup-specific variants, may actually contain only strain-specific regions. For example, the *Mycoides* B subgroup showed five subgroup-specific differences in the 16S rRNA and eleven subgroup-specific differences in 23S rRNA sequences that were not found in other subgroups (FIG. 2). However, available rRNA sequences for the *Mycoides* B subgroup currently contain only four strains for which 16S rRNA sequences were determined and two strains for 23S rRNA sequences (Table 2, 3). Among them, *B. mycoides* ATCC6462m and *B. mycoides* ATCC10206, have identical 16S and 23S rRNA sequences (FIGS. 1 and 2), as well as 16S-23S rRNA spacer, however differed with their colony morphology. If additional members of the *Mycoides* B subgroup are sequenced and added to the GenBank database, some of the subgroup-specific signatures may be actually strain-specific.

Both the 16S and 23S rRNA sequence sets showed alterations, which were present in a majority of the subgroups. Subgroups *Cereus* B, *Thuringiensis* A, *Thuringiensis* B, and *Mycoides* A all contained a C/A difference at position 1015 in their 16S rRNA sequences. The most common subgroup specific differences in 23S rRNA sequence occurred at positions 157 and 594 (Table 3, FIG. 2). The presence of these common variants among the subgroups supports a phylogenetic relationship among them.

Example 3

Grouping of Microorganisms in *B. cereus* Group According to 16S rRNA Sequences

The *B. cereus* group can be divided into seven subgroups based on 16S rRNA sequence differences (Table 2). Each of these subgroups were identified according to the name of the most common member of the subgroup: *Anthracis, Cereus* A and B, *Thuringiensis* A and B, and *Mycoides* A and B. Based on 16S rRNA sequences, an unrooted phylogenetic tree was also inferred for the *B. cereus* group using the computer program "Clustalx" (FIG. 3A). Although the affiliations in the tree are generally consistent with those defined by signature analysis (Table 2), these groupings do not correspond exactly to the current taxonomy, which divides the *B. cereus* group into seven species: *B. anthracis, B. cereus, B. thuringiensis, B. medusa, B. mycoides, B. pseudomycoides* and *B. weihenstephanensis*.

The following subgroups were described according to the 16S rRNA sequences (Table 2):

Subgroup *Anthracis* includes five strains of *B. anthracis*. These organisms do not contain any reliably established subgroup-specific or strain-specific sequence differences in comparison with the *B. anthracis* consensus sequence. Subgroup *Cereus* A includes eight members, which do not contain any subgroup-specific sequence differences from the *B. anthracis* consensus sequence, however were not classified as *B. anthracis* by conventional taxonomic methods. Of these strains, four were found to contain strain-specific sequence differences in their 16S rRNA sequences. However, three of other four strains, B. sp. strain JJ#1, *B. cereus* NCTC11143, and *B. thuringiensis* B8, were found to have sequences identical to subgroup *Anthracis* in the region of the 16S rRNA compared (about 100 nucleotides at the 3'-end of the 16S rRNA have not yet been sequenced for two of these three strains (Table 2)). Two strains of the subgroup *Cereus* A, *B. cereus* WSBC10037 and *B. cereus* 10030, have been characterized as mesophilic. As the result of the present invention, *B. cereus* HER1414, whose 16S rRNA genes are not yet sequenced, was also included in cereus A subgroup on the basis of hybridization with the microchip represented on FIG. 5B.

Subgroup *Cereus* B includes strains of *B. cereus* and *B. thuringiensis* that differ from *B. anthracis* by a C to A change at position 1015. The strains *B. cereus* NCTC9620, *B. cereus* T, *B. cereus* IAM12605, also named *B. cereus* 1771, and *B. thuringiensis* WS2626 do not differ from one another in the 16S rRNA sequence, and thus they would be indistinguishable based on 16S rRNA hybridization.

Subgroups *Thuringiensis* A and *Thuringiensis* B include strains which contain two and five subgroup-specific sequence differences respectively, C/A (1015) and C/T (192) being shared among the two subgroups. These two subgroups include mainly *B. thuringiensis* strains. Two strains in the subgroup *Thuringiensis* B (*B. thuringiensis* 4Q281 and *B. thuringiensis* IAM12077 which was also named *B. thuringiensis* NCIMB9134 or *B. thuringiensis* OSM2046) have identical 16S rRNA sequences. Two other strains within this subgroup, *B. medusa* ATCC25621 and *B. medusa* NCIMB10437, should be identical according to Bergey's Manual. However, according to sequencing (Table 2) and hybridization studies (FIG. 4), strain *B. medusa* ATCC25621 does not contain the subgroup-specific signature C/T(192), whereas according to published sequences, *B. medusa* NCIMB10437 does contain this sequence variant.

In the last two subgroups, *Mycoides* A and *Mycoides* B, five *B. mycoides* strains group in subgroup *Mycoides* A, and four fall under subgroup *Mycoides* B. Psychrotolerant strains *B. weihenstephanensis* DSM11821 and *B. cereus* strs. WSBC 10201, 10204, 10206 and 10210, which have been characterized as *B. weihenstephanensis*, were also included in subgroup *Mycoides* A. Subgroup *Mycoides* B contains *B. cereus* ki21 and *B. pseudomycoides*, which may have split off from the other two isolates (*B. mycoides* ATCC-10206 and *B. mycoides* ATCC 6462m) in this subgroup rather early in their evolution, as they have a large number of strain-specific sequence differences (Table 2).

Example 4

Grouping of Microorganisms in *B. cereus* Group According to 23S rRNA Sequences

Based on a similar analysis of 23S rRNA sequences (FIG. 2) the *B. cereus* group strains could be divided into six subgroups. These divisions were consistent with the phylogenetic tree inferred using the computer program "Clustalx" (FIG. 3B). These 23S-based subgroups correspond to six of the seven 16S-based subgroups, namely *Anthracis, Cereus* A and B, *Thuringiensis* B and *Mycoides* A and B (Tables 2 and 3). There were no 23S rRNA sequences available for any of the organisms from the subgroup *Thuringiensis* A. Therefore, based on the available data, division of the *B. cereus* group members into the specified subgroups is supported by both the 16S and 23S rRNA. Also, as with the 16S rRNA sequences, all *B. anthracis* strains had identical 23S rRNA sequences.

Subgroup *Cereus* A (Table 3) contains *B. thuringiensis* B8 and *B. cereus* NCTC11143. The 23S rRNA sequences of these two organisms include alterations at positions 594, 1559 and an insertion G(1219) (FIG. 2 and Table 3). The third member of the subgroup, *B. cereus* HER1414, whose rRNA operon is not sequenced yet, contains subgroup-specific signatures in positions 1218 and 1559. These signatures were found in the hybridization experiments disclosed herein. The third subgroup-specific signature, at position 594, was not tested for this strain. The 23S rRNA sequence of *B. cereus* WSBC10030 was sequenced only partially (FIG. 2, Table 3). It does not contain any signatures that are specific for any other subgroups, but also does not cover subgroup-specific sites for *Cereus* A subgroup. For this reason *B. cereus* WSBC10030 (Table 2 and 3) and other five strains, *B. cereus* strs. BSID723, WSBC10037, 1396 and B. sp. JJ#1 (Table 2) were placed into *Cereus* A subgroup conditionally. Final discrimination of these isolates from *Anthracis* subgroup bacteria awaits testing of the 23S rRNA sequences of these microorganisms.

*B. cereus* T, *B. cereus* NCTC9620, *B. cereus* DSM31 (also named *B. cereus* IAMI2605, *B. cereus* NCD01771) *B. thuringiensis* WS2614, and *B. thuringiensis* WS2617 were placed in subgroup *Cereus* B based on both the 16S and 23S sequence comparisons. Unfortunately, 23S rRNA sequences available for both *B. thuringiensis* strains do not extend beyond position 527 from the 5'-end of the gene.

Subgroup *Thuringiensis* B consists of three strains, *B. thuringiensis* 4Q281, *B. medusa* ATCC25621 and *B. thuringiensis* DSM2046 (also named *B. thuringiensis* IAMI207 or *B. thuringiensis* NCM9134). Sequences of the 16S rRNAs are available for all three bacteria, (Table 2). A finding from the 23S rRNA sequence analysis was the relationship between subgroups *Thuringiensis* B and *Mycoides* B. According to the 16S rRNA sequences, subgroups *Thuringiensis* B and *Mycoides* B do not share any subgroup-specific sequence signatures (FIG. 1, Table 2). However, subgroups *Thuringiensis* B and *Mycoides* B do share eight positional variants in their 23S rRNA sequences (FIG. 2, Table 3). This 23S rRNA data suggests that the organisms in these two groups may be phylogenetically related (FIG. 3B).

*B. mycoides* 2048T, *B. mycoides* MWS5303-1-4 and *B. cereus* WSBC10206 according to their 16S rRNA sequences belongs to subgroup *Mycoides* A. Unfortunately, only 527 nucleotides of sequence from the 5'-end of these 23S rRNAs are available for the last two organisms, however, they revealed enough variations to be discriminated from members of all other subgroups (Table 3, FIG. 2).

The clustering of subgroup-specific sequence variants demonstrated by the present invention provided the basis for the design of a number of diagnostic oligonucleotide probes for the identification of each of the different subgroups within the *B. cereus* group. In addition, some of the sequence variants were useful for the design of probes for the identification of individual strains.

Example 5

Design of Subgroup-Specific Probes

Results of the 16S and 23S rRNA gene sequencing indicated that microorganism identification within the *B. cereus* group would require single base mismatch discrimination. The optimal probe length was determined, taking into account the increased efficiency of mismatch discrimination which results from decreased probe length, and the increased specificity of hybridization, duplex stability, and hence hybridization signal intensity, which results from longer probes. Computer analysis of rRNA sequences available from the Ribosomal Data Project website (http://www.cme.msu.edu/RDP) indicated that 10-15 base long probes would not provide adequate specificity, the optimum probe length was determined to be 17-23 bases long.

The sequences complementary to the probes, which were selected are shown in FIGS. 1 and 2 and Table 5. The degree of matching between the probes and the rRNA sequences of the eight reference microorganisms is shown in Table 4. The location of the 16S rRNA probes on the microchip is shown in FIG. 4 and FIG. 5. The microchip on FIG. 4 includes three pairs of probes for identification of bacteria from subgroup *Thuringiensis* B (ps1/ps2, ps3/ps4 and ps5/ps6), one pair for identification of organisms from subgroups *Thuringiensis* A and B, five pairs for identification of *Mycoides* B subgroup bacteria (ps9/ps10, ps11/ps12, ps13/ps14, ps15/ps16 and ps19/ps20), and one pair for discrimination of subgroups *Anthracis, Cereus* A, and *Mycoides* B from subgroups *Cereus* B and *Thuringienses* A, B (ps17/ps18). The combined application of these probes provides a basis for distinguishing subgroup *Anthracis* from all other subgroups except *Cereus* A. Most bacteria of subgroup *Cereus* A revealed strain-specific sequence variation. Although some isolates in this subgroup have 16S rRNA sequences identical to *B. anthracis* (Table 2), these organisms do differ from *B. anthracis* in 23S rRNA sequences (FIG. 2). Therefore, probe pairs designed were ps 21/ps22 and ps23/ps24 (FIG. 2) for the discrimination of subgroups *Anthracis* and *Cereus* A using a sequence difference located respectively at positions 1559 and 1219 in the 23S rRNA molecule (Table 3).

Example 6

Identification Strategy for Subgroups and Reference Microorganisms

Eight reference organisms were selected (*B. anthracis* Ames, *B. thuringiensis* B8, *B. cereus* T, *B. cereus* 9620, *B. thuringiensis* 4Q281, *B. medusa* 25621, *B. mycoides* 6462m and *B. mycoides* 10206) to demonstrate the ability of microchips to differentiate subgroups *Anthracis, Cereus* A and B, *Thuringiensis* B and *Mycoides* B. Objectives were to determine if organisms from these closely related subgroups could be discriminated (as determined by 16S and 23S rRNA analysis), to determine if bacteria whose rRNA sequences differed by only one base could be discriminated, and to determine if *B. anthracis* could be discriminated from closely related species in the *B. cereus* group. Results of hybridization of LissRhod labeled total RNA of the reference bacteria with a microchip containing selected probes are shown in FIG. 4 and FIG. 5B.

Example 7

Identification of *B. mycoides* ATCC 6462m and *B. mycoides* ATCC 10206 (Subgroup *Mycoides* B)

The results from microchip hybridizations (FIG. 4) were identical for these two references *B. myocoides* strains. These results demonstrate the reproducibility of the microchip technique for characterizing independent isolates having identical rRNA sequences. The 16S rRNAs of *B. mycoides* 6462m and 10206 form perfect duplexes with probes ps10, ps12, ps14, ps16 and ps20 (set #1) but include mismatches with probes ps7(ps9), ps11, ps13, ps15 and ps19 (set #2). All other reference bacteria contain mismatches for set #1 probes and form perfect matches with set #2, except *B. thuringiensis* 4Q281 (subgroup *Thuringiensis* B), as well as organisms of *Thuringiensis* A subgroups, which contain one mismatch for probes ps7(ps9) and ps11 (FIG. 1 and Table 4). Microorganisms that belong to subgroup *Mycoides* A contain two mismatches with probes ps9 and ps11 and one mismatch with probe ps13 (FIG. 1).

Example 8

Identification of *B. thuringiensis* 4Q281 (Subgroup *Thuringiensis* B)

Probe pair ps7(ps9)/ps8 is specific for subgroups *Thuringiensis* A, B (FIG. 1). Probe ps8 forms a perfect match with *B. thuringiensis* 4Q281 16S rRNA and contains one or three mismatches for 16S rRNAs of all other reference bacteria. In contrast, probe ps7(ps9) contains a mismatch for *B. thuringiensis* 4Q281, and forms perfect matches with all other reference bacteria except *B. mycoides* (strains 6462m and 10206), which have two mismatches with probe ps7 (FIG. 1 and Table 4). Organisms from subgroup *Mycoides* A have three mismatches with probe ps7 (ps9) and two mismatches with probe ps8. Three probes from set #2, ps13, ps15 and ps19, form perfect match with 16S rRNA of *B. thuringiensis* 4Q281. In set #1 probe ps16 contains one mismatch, as well as probes ps14 and ps20 contain two mismatches for this bacteria.

Example 9

Differentiation of *B. medusa* ATCC 25621 and *B. thuringiensis* 4Q281

Probe pairs ps1/ps2, ps3/ps4 and ps5/ps6 are subgroup-specific for subgroup *Thuringiensis* B (FIG. 1, Table 4). Probe set #3 (ps2, ps4, and ps6) forms perfect duplexes with the 16S rRNA of *B. medusa* ATCC 25621 and *B. thuringiensis* 4Q281 and mismatches with 16S rRNAs of all other reference microorganisms. In contrast, probe set #4 (ps1, ps3 and ps5) forms mismatches with RNA isolated from *B. medusa* 25621 and *B. thuringiensis* 4Q281 and perfect matches with 16S rRNA of all five other reference bacteria. *B. medusa* 25621 and *B. thuringiensis* 4Q281 can be discriminated based on probe ps8, which forms a perfect duplex only with *B. thuringiensis* 4Q281 (FIG. 4, Table 4).

Therefore, hybridization of 16S rRNA from bacteria of the *B. cereus* group with probes from region 77-92 can be used to discriminate microorganisms of subgroup *Thuringiensis* B from bacteria of all other subgroups, and it is especially important for the discrimination between subgroups *Thuringiensis* A and B.

Example 10

Identification of *B. anthracis* Ames (Subgroup *Anthracis*)

Figure 4:
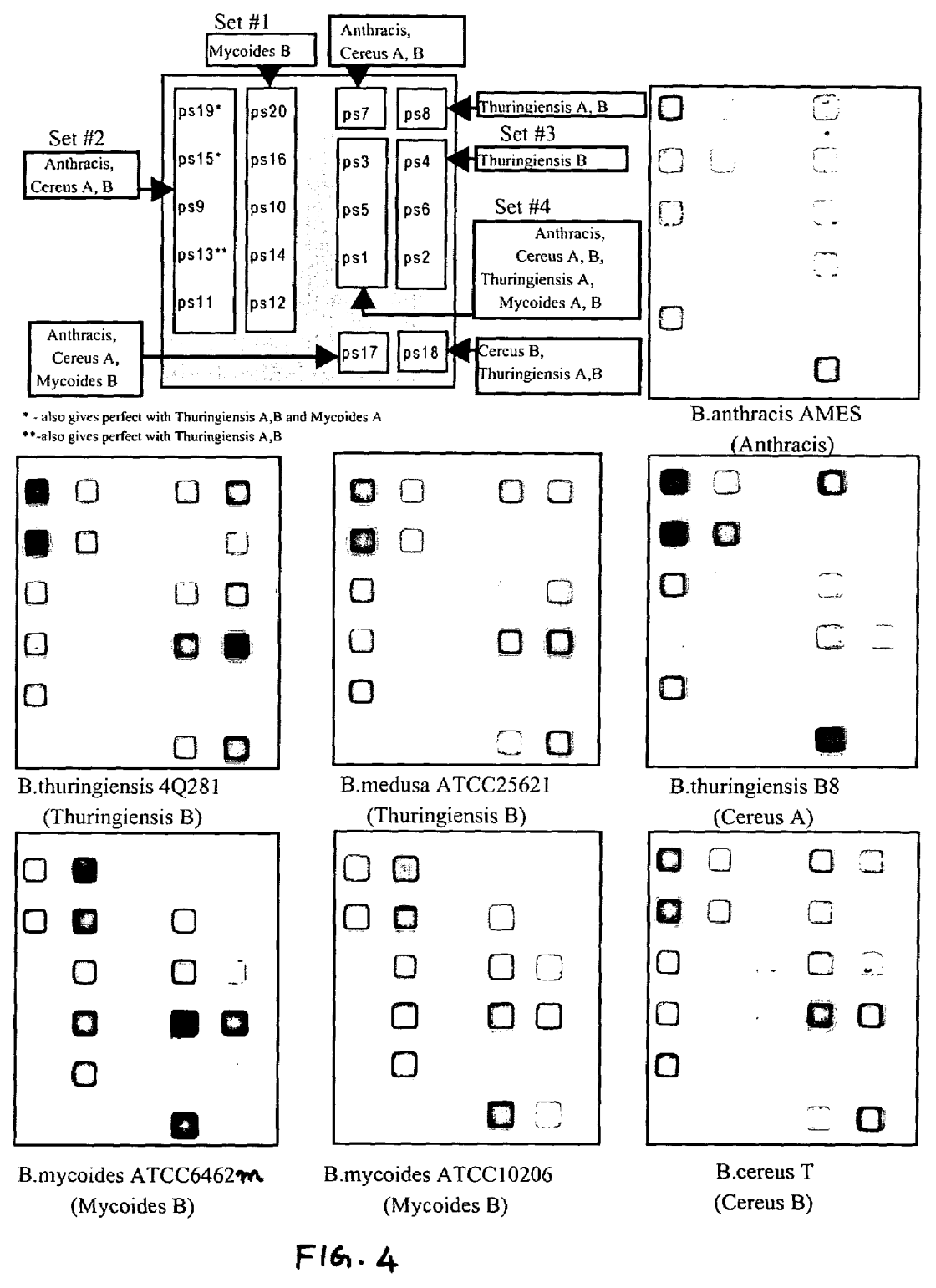

Probe ps17 is specific for subgroups *Anthracis*, *Cereus* A, and *Mycoides* B, forming perfect duplexes with 16S rRNA from *B. anthracis* Ames, *B. thuringiensis* B8 and *B. mycoides* 6462m/10206, and mismatches with all other reference microorganisms (FIG. 1 and Table 4). In contrast, probe ps18 contains a mismatch for *B. anthracis* Ames, *B. thuringiensis* B8 and *B. mycoides* ATCC 6462/ATCC10206, and is a perfect match with all other references microorganisms. Discrimination of *B. anthracis* Ames and *B. thuringiensis* B8 from *B. mycoides* ATCC 6462/ATCC10206 can be based on a "perfect" signal for probe ps17 (compare with ps18) in combination with "mismatch" signal for probe set #1 (FIG. 4, Table 4). Microorganisms of subgroup *Mycoides* A have one additional mismatch with probes ps17 and ps18.

Example 11

Identification of *B. cereus* T (Subgroup *Cereus* B)

Identification of *B. cereus* (strain T) can be established based on perfect match signals for probes ps18, ps7(ps9), and for probe sets #2 and #4 (FIG. 1, 4 Table 4).

Example 12

Identification of *B. thuringiensis* B8 (Subgroup *Cereus* A)

Organisms that belong to subgroup *Cereus* A contain 16S rRNA sequences that are identical to *B. anthracis* Ames (subgroup *Anthracis*) or that differ from *B. anthracis* Ames by strain-specific sequence variation only (Table 2). Thus, 23S rRNA sequences were used to differentiate bacteria from subgroup *Cereus* A and *B. anthracis* Ames. The 23S rRNA sequences of *B. thuringiensis* B8 and *B. cereus* NCTC11143 differ from *B. anthracis* Ames at three sites, Y/C (594), insertion G (1218-1219) and G/A (1559) (FIG. 2, Table 3). Two pairs of probes were used, ps21/ps22 and ps23/ps24 (FIG. 2) to target sites 1559 and 1219, respectively. Probes ps21 and ps23 form a perfect duplex with the 23S rRNA of *B. anthracis* Ames but not *B. thuringiensis* B8 and *B. cereus* NCTC11143 23S rRNA. Probes ps22 and ps24 provide complementary information, by having a mismatch with *B. anthracis* Ames 23S rRNA and being complementary to *B. thuringiensis* B8 and *B. cereus* NCTC11143 23S rRNAs (FIGS. 2, 5A). The discriminative feasibility of 23S rRNA probes ps21/ps22 and ps23/ps24 was tested by using *B. cereus* HER1414, whose rRNA genes were not sequenced. *B. cereus* HER1414 and *B. anthracis* Sterne revealed the same hybridization pattern after hybridization with a 16S rRNA microchip (FIG. 5B, ps18/ps17 shown only). A set of 23S rRNA probe pairs ps21/ps22 and ps23/ps24 successfully discriminated *B. cereus* HER1414 and *B. thuringiensis* B8 from *B. anthracis* Sterne with the hybridization signal ratio for these two pairs being 0.7, 0.4, 2.2 and 0.7, 0.4, 1.7, respectively (FIG. 5B).

Example 13

Identification of Polymorphic Sites

Partial (about 80% of total) sequencing of the *B. anthracis* Ames genome (TIGR website http://www.tigr.org) indicated that organisms from the *B. cereus* group may contain at least ten copies of the rRNA operon. Considerable polymorphism of these genes at some sites (for example 1:1 ratio of C:T at position 594 of 23S rRNA) has been demonstrated (TIGR website http://www.tigr.org). Sequencing revealed two polymorphic sites in the 23S rRNA molecule at positions 594 and 1559 for a number of microorganisms of the *B. cereus* group (FIG. 2 and Table 3). For example *B. cereus* T, *B. thuringiensis* 4Q281 and *B. cereus* 9620 have polymorphisms in their 23S rRNA genes at site 1559 with G:A ratios equal to 1.5:1, 1:1 and 1:3.5, respectively. At the same time, *B. anthracis* Ames and *B. mycoides* 10206 have a G in this site, and *B. thuringiensis* B8 has an A in this position (FIG. 2). The possibility of recognizing polymorphisms in this site was demonstrated by using a pair of probes, ps21/ps22. For these probes the hybridization signal ratio for *B. cereus* T, *B. thuringiensis* 4Q281 and *B. cereus* 9620 have been found to be intermediate (1.0, 0.72 and 0.64, respectively) between *B. anthracis* Ames, or *B. mycoides* 10206 (1.8 and 1.5, respectively) and *B. thuringiensis* B8 (0.45) (FIG. 5A).

Example 14

Identification of Mixtures

The 16S rRNA of *B. cereus* 9620 and *B. anthracis* Ames differ from each other in only one nucleotide. Nevertheless, not only homogeneous samples of these bacteria were discriminated, but also mixtures of RNA from these two microorganisms (FIG. 6A). The ratio of probes ps17/ps18, species-specific to these bacteria, is 1:3 for *B. cereus* 9620 and 8:1 for *B. anthracis* Ames. A 2:3 mixture of RNA from *B. cereus* 9620 and *B. anthracis* Ames, respectively, revealed 3:2 ratio (FIG. 6A). Identification of 10:1 mixture of *B. thuringiensis* B8 RNA and *B. thuringiensis* 4Q281 RNA were demonstrated. The identification of microorganisms and their relative content in the mixture was determined using three pairs, ps5/ps6, ps7/ps8, and ps17/ps18 (FIG. 6B). The signal changes were different for different probe pairs. For correct estimation of the percentage in the mixture, a calibration would be required for each pair separately. Even without quantitative interpretation of the results variance from the expected hybridization ratios suggests the presence of both target groups.

Example 15

Cross-Hybridization of Selected Probes with Non-Target Bacteria

The number of subgroup-specific differences in rRNA sequences for bacteria from the *B. cereus* group are few and localized. This creates difficulties in the selection of probes specific to individual subgroups of bacteria. For example, the sequences of two of the twenty probes on the microchip (ps17 and ps20) (FIG. 1) selected for identification of *B. cereus* group reference microorganisms also match the 16S rRNA sequences of a number of bacteria that belong to other groups of the genus *Bacillus*. The use of probes targeting the entire *B. cereus* group and for some other groups may resolve this problem. To demonstrate this, probe ps25 was designed to match all known sequences of *B. cereus* microorganisms and probe ps26 to target the *B. subtilis* group (*B. subtilis, B. amiloliquifaciens, B. lentimorbus, B. popilliae,* and *B. atrophaeus*). Hybridization analysis indicated that these probes effectively differentiated *B. subtilis* B-459 from *B. anthracis* Ames, *B. cereus* T, *B. mycoides* 10206, and *B.*

*thuringiensis* 4Q281 (FIG. 7). Thus, the *B. cereus* group probes can be used as an internal check to validate probes ps17 and ps20.

Materials and Methods

Bacterial Strains

Ten strains belonging to the *B. cereus* group: *B. anthracis* str. Ames ANR, *B. anthracis* str. DeltaAmes-1, *B. thuringiensis* str. B8, *B. cereus* str. NCTC9620, *B. cereus* str. T, *B. thuringiensis* str. 4Q281, *B. medusa* str. ATCC25621, *B. mycoides* str ATCC6462m, and *B. mycoides* str. ATCC10206 (Table 2) were obtained from Dr. John Ezzell, USAMRIID (The U.S. Army Medical Research Institute of Infectious Diseases, Fort Detrick, Md.). Two of these strains were isolated as an occasional admixture from a culture previously identified as *B. mycoides* str. ATCC6462, revealed different colony morphology and received strain numbers, *B. mycoides* str. ATCC6462m and *B. mycoides* str. ATCC10206.

Sequencing of 16S and 23S rRNA Genes

Total DNA was isolated from frozen cell pellets by the guanidine extraction method. 16S rDNA and 23S rRNA were amplified from total genomic DNA for 10 strains. For each amplification reaction, 0.1 µg of bacterial DNA was subjected to PCR in a total volume of 100 µl, with 2.5 units of Taq polymerase (Perkin-Elmer, Boston, Mass.), 50 mM KCl, 10 mM Tris-HCl pH 8.3, 1.5 mM MgCl2, 0.01% (w/v) gelatin, 200 µM of each dNTP (dATP, dCTP, dGTP, TTP), and 6 µM of each of two primers. The primers used for 16S rDNA and 23S rDNA amplification are listed in Table 1. The thermal profile included denaturation at 94° C. for 2 min, primer annealing at 45° C. for 2 min, and extension at 72° C. for 2 min and then 35 cycles of denaturation at 94° C. for 15 sec, primer annealing at 45° C. for 15 sec, and extension at 72° C. for 4 min. DNA was purified using QIAquick PCR Purification Kit (QIAGEN Inc., Valencia, Calif.) and purified PCR products were directly sequenced by the cycle sequencing method using AmpliTaq DNA polymerase FS (Perkin-Elmer, Boston, Mass.), fluorescently labeled dye-terminators, and 373A fluorescent sequencer (ABI; Perkin-Elmer, Boston, Mass.). Sequencing primers are shown in Table 1.

Development of Expanded Sequence Databases

All 16S and 23S rRNA sequences for members of the *B. cereus* group available in GenBank were retrieved. Thirty-three 16S rRNA sequences obtained from the GenBank database and one from "The Institute of Genomic Research (TIGR) were aligned with eleven 16S rRNA sequences independently determined herein, including one *B. anthracis* strain (Sterne) resequenced is part of the invention (Table 2). Software developed in the inventors' lab was used for comparative analysis and probe design.

Six complete and five partial sequences of 23S rRNA for *B. cereus* group bacteria were obtained from GenBank and TIGR. These were aligned with nine additional 23S rRNA sequences for the *B. cereus* group determined in this study and one *B. anthracis* strain (Sterne) resequenced as part of the invention (Table 3).

Creation of Phylogenetic Tree

The 16S and 23S rRNA sequence databases were also used to create an unrooted phylogenetic tree for all of the strains in the database. These trees were created using the multiple sequence alignment computer program "Clustalx". All positions of nucleotides in analyzed alignment of sequences, where unidentified nucleotides N were found, were excluded from consideration for all microorganisms whose sequences were included in the alignment.

Design of Oligonucleotide Probes

The following strategy was used for the probe design. Each unique 16S rRNA sequence was used to create a set of all 20-mer oligonucleotides possible for that sequence (the set consisted of L-19 overlapping oligonucleotides, where L denotes the length of the entire 16S rRNA sequence). Each of these 20-mer overlapping oligonucleotides was then considered as a potential probe. Each potential probe was tested against all available 16S rRNA sequences (GenBank and RDP) by an algorithm that estimates the relative duplex stability according to the number and position of mismatches. If the 16S rRNA of any microorganism that did not belong to the target group (genus, species, or subgroup) of interest formed stable duplexes with any oligonucleotide considered as a potential probe for the microchip, this oligonucleotide was excluded from the list of probes, except probes ps17 and ps20 specifically mentioned in Example 15.

Oligonucleotide Microchip Design and Construction

DNA microchips were constructed with ten or 31 pairs of oligonucleotide probes targeting 16S rRNA and 23S rRNA sequences (see FIG. 1 and FIG. 8) and two group-specific probes (ps25 and ps26), two pairs of oligonucleotide probes targeting 23S rRNA sequences (ps21 and ps22, see FIG. 2) except probe ps26 which was 19 bases long. Each probe was 20 bases long. Oligonucleotides were synthesized on an automatic DNA/RNA synthesizer (Applied Biosystems 394) using standard phosphoramide chemistry. 5'-Amino-Modifier C6 (Glen Research, Sterling, Va.) was linked to the 5'-end of the oligonucleotides. A micromatrix containing 100- by 100- by 20 µm polyacrylamide gel pads fixed on a glass slide and spaced 200 µm from each other was manufactured by photopolymerization, and activated as described herein. Six nl of individual 1 mM amino-oligonucleotide solutions was applied to each gel pad containing aldehyde groups according to the procedure described below.

Determination of Relative Duplex Stability

To determine the relative duplex stability wherein the amount of positions where the microorganisms may be differentiated was restricted, and were tested all positions synthesizing all reasonable oligo pairs around each site of differentiation, oligos were applied onto the chip and hybridized with labeled RNA from appropriate microorganisms. Pairs of oligos that revealed the highest signal in combination with highest perfect signal/mismatch signal ratio were selected.

Preparation of Acrylamide Micro-Matrices by Photo-Polymerization

Preparation of Glass Slides
1. Immerse 10 glass slides in 10 M sodium hydroxide in a Wheaton glass-slide container (volume 150 ml) for 30 minutes.
2. Rinse with five changes of double-distilled water in a container.
3. Immerse 10 slides in concentrated sulfuric acid in container for 30 minutes
4. Rinse five times in double-distilled water and allow to stand in double distilled water for 5 minutes then rinse again.
5. Remove water drops with nitrogen stream. Dry for 1 h at 60° C.

Treatment of Cleaned Slide with Bind Silane.

Immerse slides in 3-(Trimethoxysilyl)propyl methacrylate and incubate for 40 h min at 37° C.

Rinse thoroughly with ethanol and then double-distilled water and dry under a nitrogen stream.

Preparation of Solutions for Aldehyde Matrices
1. Composition of 5% polyacrylamide solution 0.5 ml 40% Acrylamide/Bis solution (19:1) 1.82 ml 0.2M sodium phosphate buffer (consists of equal volumes of 0.2M sodium phosphate monobasic monohydrate and 0.2M sodium phosphate dibasic anhydrous pH=6.8, store at 4° C.).
1.6 ml glycerol
0.08 ml monomer I solution (N-(5,6-di-O-isopropylidene) hexyl acrylamide). For monomer I solution add 1 ml MilliQ water to aliquot of monomer I stock (25 mg) located in −80° C. freezer. Aliquot and store these at −20° C. for approximately 1 month.
2. filter.
3. Prepare solution weekly and store at 4° C. Allow solution to reach room temperature before use.

Assembly of Gel-Casting Cassette.
1. Clean mask surface with ethanol.
2. Rinse thoroughly with distilled water stream rubbing briskly with lint-free tissue.
3. Dry under a nitrogen stream.
4. Place spacers (audio tape film) on chrome side of mask; two spacers from both sides and one in the center.
5. Place slide over mask and spacers with treated surface facing mask.
6. Clamp in place.

Photo-Polymerization (Optimized for 4-Cluster Mask).
Prepare mixture: 100 µl of above polyacrylamide solution
0.4 µl Methylene blue (0.04%)
1.2 µl TEMED
Vortex 3 seconds
Degas solution 3 min
1. Pipette mixture between the slide and the mask allowing the solution to move between the space by capillary action. Take care that air does not enter the pipette or space. Pipette off excess solution.
2. Turn cassette over so that glass slide is underneath the mask. Place in Oriel chamber.
3. Irradiate for 300 sec.
4. Carefully disassemble the cassette under water using the point of a scalpel to separate the slide and mask (the slide floats free without pressure being placed on the gel elements.) Take care not to scratch mask.
5. Rinse 30 seconds under running distilled water and soak in distilled water for 15 minutes
6. Air dry in a laminar-flow hood
7. Keep in dust-free slide box at room temperature. Matrices can be kept for at least 1 year.

Procedure for Activation (Deprotection) of Aldehyde Matrices
1. Place matrix in 2% trifluoro-acetic acid for 10 minutes at room temperature (prepare fresh solution after every 10 microchips).
2. Rinse well (5 or 6 times) with filtered distilled water for 1 min
3. Wash in distilled water X3 times then leave 3-5 mins in last rinse and dry 20 min in air.
4. Put slide into Repel Silane™ (use fresh solution for each treatment) for one minute.
5. Wash with acetone or dichloromethane (15 sec) and then thoroughly with tap-distilled water (15 sec under stream).
6. Load oligonucleotides.
7. Put microchip into freshly prepared solution of pyridine-borane complex in chloroform (0.1M)(80 ml chloroform/1 ml pyridine borane) and cover chloroform layer with water; (approx ¼ inch) hold 12 hours at room temperature (O. N.)
8. Wash microchip with distilled water.
9. Place microchip into 0.1M sodium borohydride on microchip for 20 min.
10. Wash with distilled water 1 min.
11. Heat microchip in 0.1×SSPE with 0.1% SDS at 60° C. for 1 h (50 ml).
12. Wash biochip in Hybridization Station for 15 min on a stirrer.
13. Wash with distilled water 1 min.
14. Dry microchip in a dust-free environment in the air for 20 min.
15. The chip is now ready for hybridization. The chip could be kept at room temperature.

Standardized Sources of Chemicals and Equipment
1. DEPC-Treated Water (Ambion, cat#9920)
2. 0.5M EDTA, pH 8.0 (Ambion, cat#9260G)
3. Eppendorf Centrifuge 5417C (Fisher, cat#05-406-11)
4. Eppendorf microcentrifuge tubes, 1.5 ml (Fisher, cat#05-402-24B)
5. Acetone (Sigma, cat#A4206)
6. Guanidine Thiocyanate (Fisher, cat#BP221-1)
7. 1M HEPES (Sigma, cat#H4034)
8. Hybridization chamber: Probe-Clip Press-Seal Incubation Chamber (Sigma, cat#Z36,157-7)
9. Kimwipes (Fisher, cat#06-666A)
10. 20×SSPE (Sigma, cat#S2015)
11. Tween 20 (Fisher, cat#BP337-100)
12. Imaging Chamber (Sigma, cat#Z36,585-8)
13. Ultrafree-MC 0.45 µm filter unit (Millipore, cat#UFC30HVNB)
14. Triton X-100 (Sigma, cat#T9284)
15. Ethyl Alcohol, absolute 200 proof, 99.5%, A.C.S. reagent (Aldrich, cat#45,984-4)
16. QIAquick PCR Purification Kit (50) (Qiagen, cat#28104)
17. Taq DNA Polymerase (includes 10×PCR reaction buffer) (Amersham Pharmacia Biotech, cat#T0303Z)
18. PCR Nucleotide Mix: PCR nucleotide mix (10 mM each dATP, dCTP, dGTP, dTTP) (Amersham Pharmacia Biotech, cat# US77212)
19. Sonicated Salmon Sperm DNA, Phenol Extracted (Amersham Pharmacia Biotech, cat#27-4565-01)
20. Albumin from bovine serum, 20 mg/ml in water (Sigma, cat#B8667)
21. Luer Lok syringe, 60 cc/2 oz, B-D (Fisher cat#14-823-2D)
22. Millex-GN 0.20 filter units (Millipore, cat#SLGN025NS)

An example of a customized microchip is shown in FIG. 8 and Table 5.

RNA Isolation

Total RNA was isolated from frozen cell pellets of eight *B. cereus* group bacteria: *B. anthracis* Ames, *B. thuringiensis* B8, *B. cereus* T, *B. cereus* 9620, *B. thuringiensis* 4Q281, *B. medusa* 25621, *B. mycoides* 6462m and *B. mycoides* 10206. Cells were lysed by bead beating the cell pellet (approx. 0.2 g) in the presence of 0.5 g baked zirconium oxide beads (0.1 mm), 500 μl phenol (pH 5.1), 500 μl 0.1 M sodium acetate, pH 5.1, and 50 μl 20% SDS at high speed for 2 min, followed by incubation at 65° C. for 10 minutes and an additional bead-beating step for 2 minutes at high speed. RNA was isolated by phenol extraction and precipitated by addition of 0.5 volumes of 7.5 M ammonium acetate and 2.5 volumes of ethanol. Following storage at −80° C.

overnight the RNA was recovered by centrifugation at 14,000 rpm for 5 min, washing the RNA pellets two times with ethanol, and resuspending in diethyl pyrocarbonate (DEPC)-treated H2O.

Magnesium-Sodium Periodate Fragmentation of RNA and Dye Labeling

RNA (10 to 20 μg) and DEPC treated H20 were combined and preheated at 95° C. for 5 min. MgCl2 was added to 60 mM (total volume 20 μl) and the reaction solution was heated at 95° C. for 40 min. Phosphatase treatment was carried out by addition of 3 μl 10× alkaline phosphatase buffer (Promega, Madison, Wis.) and 0.2 μl alkaline phosphatase (1 U/μl) (Promega, Madison, Wis.) and heating at 37° C. for 30 min. Oxidation of the 3'-end ribose moiety was conducted by addition of 6.5 Pl of 100 mM sodium periodate and incubation at room temperature for 20 min. Labeling was carried out by addition of 3.5 μl of 100 mM Lissamine rhodamine B ethylenediamine (LissRhod) (Molecular Probes, Eugene, Oreg.), 1.65 μl of 1 M HEPES (pH 7.5) and heating at 37° C. for 1 h. Reduction of Schiff base was conducted by addition of 6.7 μl of 200 mM sodium cyanoborohydride and incubation at room temperature for 30 min. Labeled RNA was precipitated by addition of 15 volumes of 2% lithium perchlorate in acetone and storage at −20° C. for 20 min. After centrifugation at 14,000 rpm for 5 min, RNA pellets were washed twice with acetone and dried at 55° C. for 10 min.

Excess LissRhod was removed from RNA by butanol treatment: RNA pellets were suspended in 300 μl DEPC-treated H2O, and samples were concentrated to 60 μl by removal of water with butanol. Treatment was repeated until butanol was free of color. RNA was precipitated in 2% LiClO4 in acetone at −20° C. for 20 min. After centrifugation at 14,000 rpm for 5 min, RNA pellets were washed twice with acetone, dried at 55° C. for 10 min, and suspended in 10 to 20 μl DEPC treated H2O.

Hybridization with Microchips

The 35 μl of hybridization solution containing 0.1 to 1 μg fragmented and labeled RNA, 1M guanidine thiocyanate (GuSCN), 5 mM EDTA, and 40 mM HEPES (pH 7.5) was passed through a 0.22μ filter to remove particulates, then heated at 95° C. for 3 min and placed on ice. Thirty μl of the hybridization solution was added to a hybridization chamber (Grace Biolabs, Bend, Oreg.), and the hybridization chamber was affixed to a microchip. The microchip was allowed to hybridize overnight at room temperature in the dark. After hybridization, the chamber and hybridization solution were removed from the microchip, and the microchip washed twice for 10 sec each with 100 μl washing buffer. Washing buffer consisted of 0.9 M NaCl, 50 mM sodium phosphate (pH 7.0), 6 mM EDTA, and 1% Tween 20.

Hybridization Data Analysis

After hybridization the microchips were analyzed with a custom made wide-field-high-aperture fluorescence microscope (Vavilov State Optical Institute, St. Petersburg, Russia) equipped with a cooled CCD camera (Princeton Instruments, Acton, Mass.), a thermal table, and XY positioners, and operated with a computer with specially designed software. Parameters of the microscope are as follows: field of view 4 mm by 4 mm, aperture 0.4, working distance 12 mm. Up to 144 individual gel elements with the size of 100- by 100- by 20 μm spaced by 100 μm may be analyzed in parallel in one field of view. Images were captured with WinView Software (Princeton Instruments). The hybridization data was quantified from the WinView image using software (Lab View, version 4.0.1 and MicroChip Imager, Oleg Alferov).

Table 1. Primers used for PCR and for sequencing of 16S and 23S rRNA genes of B. cereus groups bacteria [a]. (SEQ ID NOS 27-56, respectively, in order of appearance)

TABLE 1

Primers used for PCR and for sequencing of 16S and 23S rRNA genes of B. cereus groups bacteria[a]. (SEQ ID NOS 27-56, respectively, in order of appearance)

| Name | Sequence | Location |
|---|---|---|
| P1 | 5' - GTT TGA TCC TGG CTC AG | 11-27 (16S rRNA) |
| P10 | 5' - CCA GTC TTA TGG GCA GGT TAC | 136-116 (16S rRNA) |
| P11 | 5' - TCC ATA AGT GAC AGC CGA AGC | 226-206 (16S rRNA) |
| P5 | 5' - CTA CGG GAG GCA GCA GTG GG | 340-360 (16S rRNA) |
| P3 | 5' - GWA TTA CCG CGG CKG CTG | 535-517 (16S rRNA) |
| P2 | 5' - GGA TTA GAT ACC CTG GTA GT | 784-803 (16S rRNA) |
| P6 | 5' - CCG TCA ATT CCT TTR AGT TT | 926-907 (16S rRNA) |
| P8 | 5' - TTC GGG AGC AGA GTG ACA GGT | 1029-1049 (16S rRNA) |
| P9 | 5' - TAC ACA CCG CCC GTC ACA CCA | 1392-1412 (16S rRNA) |
| P4 | 5' - RGT GAG CTG TTA CGC | 1513-1492 (16S rRNA) |
| Pr1 | 5' - CCG AAT GGG GVA ACC C | 114-129 (23S rRNA) |
| Pr13 | 5' - CCG TTT CGC TCG CCG CTA CTC | 262-242 (23S rRNA) |
| PB1 | 5' - TAG TGA TCG ATA GTG AAC CAG | 485-505 (23S rRNA) |
| Pr2 | 5' - CAT TMT ACA AAA GGY ACG C | 621-603 (23S rRNA) |
| Pr3 | 5' - GCG TRC CTT TTG TAK AAT G | 603-621 (23S rRNA) |
| PB2 | 5' - TAG TGA TCG ATA GTG AAC CAG | 755-736 (23S rRNA) |
| PB3 | 5' - TAG TGA TCG ATA GTG AAC CAG | 969-990 (23S rRNA) |
| Pr4 | 5' - RGT GAG CTR TTA CGC | 1151-1137 (23S rRNA) |
| Pr5 | 5' - WGC GTA AYA GCT CAC | 1136-1150 (23S rRNA) |
| PB4 | 5' - CAT ACC GGC ATT CTC ACT TC | 1308-1289 (23S rRNA) |
| PB5 | 5' - ACA GGC GTA GGC GAT GGA C | 1408-1426 (23S rRNA) |
| PB8 | 5' - AAC CTT TGG GCG CCT CC | 1679-1661 (23S rRNA) |
| Pr6 | 5' - CYA CCT GTG WCG GTT T | 1673-1659 (23S rRNA) |
| Pr7 | 5' - AAA CCG WCA CAG GTR G | 1659-1673 (23S rRNA) |
| Pr8 | 5' - CAY GGG GTC TTT RCG TC | 2092-2076 (23S rRNA) |
| Pr9 | 5' - GAC GYA AAG ACC CCR TG | 2076-2092 (23S rRNA) |
| Pr10 | 5' - GAG YCG ACA TCG AGG | 2535-2521 (23S rRNA) |

TABLE 1-continued

Primers used for PCR and for sequencing of 16S and 23S rRNA genes of *B. cereus* groups bacteria*[(a)]. (SEQ ID NOS 27-56, respectively, in order of appearance)

| Name | Sequence | Location |
|---|---|---|
| Pr11 | 5' - CCT CGA TGT CGR CTC | 2521-2535 (23S rRNA) |
| Pr12 | 5' - GYT TAG ATG CYT TC | 2783-2770 (23S rRNA) |
| R1 | 5' - GGC GGC GTC CTA CTC TCA C | 112-95 (5S rRNA) |

[(a)]primers P1-P4, Pr1-Pr7 and R1 were used for DNA amplification. All other primers were utilized for sequencing. Primers P8, P9, P10 and P11 were selected de novo, other primers were described previously.

TABLE 2

Classification of bacteria in the *Bacillus cereus* group according to 16S rRNA sequences

| Subgroup name | Subgroup-specific signatures (position)[(*)] | Start and end of sequence | Organism | GenBank AC | Positions of strain-specific variations |
|---|---|---|---|---|---|
| *Anthracis* | Consensus | 11-1556 | *B. anthracis str. Ames ANR*[a,e] | AF155950, TIGR[g] | — |
| | | 11-1556 | *B. anthracis str. DeltaAmes-1*[b] | AF155951 | — |
| | | 11-1556 | *B. anthracis str. Sterne*[d] | AF176321[a] | — |
| | | 1-1453 | *B. anthracis str. Sterne* | X55059 | del C(942)[b] |
| | | 61-528, 815-1503 | *B. anthracis str. 1* | *** | — |
| | | 61-528, 815-1503 | *B. anthracis str. 2* | *** | — |
| *Cereus* A | Consensus | 11-1556 | *B.thuringiensis str. B8*[a,e] | AF155955 | — |
| | | 1-1453 | *B. cereus str. NCTC11143* | X55063 | — |
| | | — | *B. cereus str. HER1414*[f] | — | ? |
| | | 31-1464 | *B. sp. str. JJ#1*[h] | Y15466 | — |
| | | 28-1536 | *B. sp. str. BSID723*[h] | AF027659 | 1232 |
| | | 49-1524 | *B. cereus str. WSBC10037*[h] | Z84576 | 178 |
| | | 49-1524 | *B. cereus str. WSBC10030*[h] | Z84575 | 353, 600, 864, 1146 |
| | | 28-1515 | *B. cereus str. 1396*[h] | AF206326 | 181, 467, 480, 482, 590, 995, 1146, 1244, 1345 |
| *Cereus* B | *C/A(1015)* | 11-1556 | *B.cereus str. NCTC9620*[a,e] | AF155952 | — |
| | | 11-1556 | *B.cereus str. T*[a,e] | AF176322 | — |
| | | 28-1515 | *B. cereus str. IAM12605* | D16266 | — |
| | | 1-1453 | *B. cereus str. NCD01771* or *DSM31* | X55060 | — |
| | | 49-1524 | *B. cereus str. ATCC27877* | Z84581 | 828 |
| | | 26-1183 | *B. cereus* | AF076031 | 498, 520, 523, 829, 1167 |
| | | 49-1524 | *B. thuringiensis str. WS2614* | Z84584 | 127 |
| | | 49-1524 | *B. thuringiensis str. WS2617* | Z84585 | 1153 |
| | | 49-1524 | *B. thuringiensis str. WS2618* | Z84586 | 725 |
| | | 49-1524 | *B. thuringiensis str. WS2626* | Z84588 | — |
| *Thuringiensis* A | *C/A(1015)* | 49-1524 | *B. thuringiensis str. WS2623* | Y18473 | 109, 679, 1228, 1505 |
| | C/T(192) | 49-1524 | *B. thuringiensis str. WS2625* | Z84587 | 565, 1183 |
| *Thuringiensis* B | *C/A(1015)* | 11-1556 | *B.thuringiensis str. 4Q281*[a,e] | AF155954 | — |
| | C/T(192) | 11-1556 | *B.medusa str ATCC25621*[a,c,e] | AF155958 | no C/T(192) |
| | A/G(77), T/C(90), | 11-1556 | *B. medusa str. NCIMB10437*[c] | X60628 | 1038, 1383 |
| | T/A(92) | 28-1515 | *B. thuringiensis str. IAM12077* or *DSM2046* | D16281 | — — |
| | | 1-1453 | *B. thuringiensis str. NCIMB9134* or *DSM2046* | X55062 | 182, 186, 187, 769, 822, 823, 1281, 1282, 1283, 1301, 1429, 1430, 1463, 1464, 1475, 1476, 1478, 1479 |
| | | 7-1552 | *B. sp. str. Termite isol. 'bac'* | X81132 | |
| *Mycoides* A | *C/A(1015)* | 1-1453 | *B. mycoides str. DSM2048*[d] | X55061 | — |
| | C/T(192) | 49-1556 | *B. mycoides str. MWS5303-1-4* | Z84591 | 1456 |
| | G/A(133), C/T(182), G/A(197), A/G(286) | 49-1526 | *B. mycoides str. DRCI* | AF144645 | 63, 1279, 1319-1321, 1398, 1439, 1443, 1473, 1479, 1484 |
| | C/T(1019), | 49-1524 | *B. mycoides str. MWS5303-2-51* | Z84583 | 180 |
| | G/A(1030), | 32-1546 | *B. mycoides str. ATCC6462*[d] | AB021192 | — |
| | T/A(1464) | 14-1546 | *B. weihenstephanensis DSM11821* | AB021199 | — |
| | | 49-1524 | *B. cereus str. WSBC10201* | Z84577 | 203, no A/G(286), 1515 |
| | | 49-1524 | *B. cereus str. WSBC10204* | Z84578 | 128 |
| | | 49-1524 | *B. cereus str. WSBC10206* | Z84579 | 225, 1519, 1520 |
| | | 49-1524 | *B. cereus str. WSBC10210* | Z84580 | 60, 375, 1298 |

TABLE 2-continued Classification of bacteria in the *Bacillus cereus* group according to 16S rRNA sequences

| Subgroup name | Subgroup-specific signatures (position)(*) | Start and end of sequence | Organism | GenBank AC | Positions of strain-specific variations |
|---|---|---|---|---|---|
| *Mycoides* B | A/C(189), T/G(200), G/C(208), T/C(1036), A/G(1045) | 11-1556 | B.mycoides str ATCC6462m[a,e] | AF155956 | — |
| | | 11-1556 | B.mycoides str ATCC10206[a,e] | AF155957 | — |
| | | 34-1374 | B. cereus str. Ki21 | AJ288157 | 95, no T/G(200), 202, 329, 752, 778, 793, no T/C(1036), 1350, 1360, 1374 |
| | | 7-1538 | B. pseudomycoides sp. nov. | AF013121 | 55, 341, 495, 516, 566, 929, 1017, 1104, 1110, 1121, 1128, 1138 |

(*)for more details see FIG. 1.
[a]sequenced in this work.
[b]need to be reexamined, see also Results.
[c]according to Bergey's Manual, these two strains of B. medusa should be identical. This was not confirmed with 16S rRNA sequencing.
[d]according to Bergey's Manual, these two strains of B. mycoides should be identical.
[e]strains selected in this study as reference organisms to demonstrate subgroup identifications.
[f]not sequenced, identified in this study by 16S/23S rRNA oligonucleotide microchip analysis (see Results).
[g]partial (about 90%) sequences of whole B. anthracis Ames genome, data of TIGR (http://www.tigr.org).
[h]final discrimination from Anthracis subgroup will be done after testing 23S rRNA gene sequence (see Results).
***J. Jackman, unpublished.
Subgroup-specific mutations, which are highlighted in bold, are identical for two or more subgroups and were placed on separate lines to demonstrate connections between different subgroups.

TABLE 3

Classification of bacteria in the *Bacillus cereus* group according to 23S rRNA sequences

| Subgroup name | Subgroup-specific signatures (position)(*) | Start and end of sequence | Organism | GenBank AC | Positions of strain-specific variations |
|---|---|---|---|---|---|
| *Anthracis* | Consensus | 1-2922 | B. anthracis str. Ames ANR[a,d] | AF267734[a], TIGR[b] | — |
| | | 1-2922 | B. anthracis str. DeltaAmes-1[a] | AF267876 | — |
| | | 1-2922 | B. anthracis str. Sterne[a] | AF267877[a] | — |
| | | 15-2943 | B. anthracis str. Sterne | S43426 | (491)[e], del(1413, 1414)[e], (2651)[f] |
| *Cereus* A | Y/C(594) | 1-2923 | B.thuringiensis str. B8[a,d] | AF267880 | — |
| | G/A(1559) | 1-2923 | B. cereus str. NCTC11143 | X64646 | — |
| | Insertion G(1218-1219) | 1-527 | B. cereus str. WSBC10030[f] | Z84589 | — |
| | | — | B. cereus str. HER1414[e] | — | ? |
| *Cereus* B | Y/C(594) | 1-2922 | B.cereus str. NCTC9620[a,d] | AF267878 | — |
| | G/R(1559) | 1-2922 | B.cereus str. T[a,d] | AF267879 | — |
| | T/A(2153) | 1-2787 | B. cereus str. DSM31 or IAM12605 or NCD01771 | X94448 | (1275), (1559) |
| | | 1-527 | B. thuringiensis str. WS2617[f] | Z84594 | — |
| | | 1-527 | B. thuringiensis str WS2614[f] | Z84593 | — |
| *Thuringiensis* B | Y/C(594) | 1-2922 | B.thuringiensis str. 4Q281[a,d] | AF267881 | (1559) |
| | T/C(157) | 1-2922 | B.medusa str. ATCC25621[a,d] | AF267885 | — |
| | G/A(921), A/G(1020), C/T(1037), G/A(1209), A/G(1251), T/C(1283) | 1-2784 | B. thuringiensis str. DSM2046 or IAM12077 or NCIMB9134 | X89895 | (57), (413), ins(479-480), del(541-542), (646), (670), (1953), (2055), ins(2556-2557), del(2573) |
| | C/T(132), A/T(174) | | | | |
| | T/A(2153) | | | | |
| | G/T(1250) | | | | |
| *Mycoides* A | T/C(157) | 1-527 | B. mycoides str. 2048T | Z84592 | — |
| | CA/TC(256,266), GT/AC(364,365) | 1-527 | B. mycoides str. MWS5303-1-4 | Z84591 | — |
| | C/T(132), A/T(174) | 1-527 | B. cereus str. WSBC10206 | Z84590 | — |
| | C/T(375) | | | | |
| *Mycoides* B | Y/T(594) | 1-2922 | B.mycoides str. ATCC6462m[a,d] | AF267884 | — |
| | T/C(157) | 1-2922 | B.mycoides str. ATCC10206[a,d] | AF267883 | — |
| | G/A(921), A/G(1020), C/T(1037), G/A(1209), A/G(1251), T/C(1283) CA/TC(265,266), GT/AC(364,365) GA/AG(346, 347), TC/CT(358, 359), C/A(482), C/T(672), | | | | |

TABLE 3-continued

Classification of bacteria in the *Bacillus cereus* group according to 23S rRNA sequences

| Subgroup name | Subgroup-specific signatures (position)(*) | Start and end of sequence | Organism | GenBank AC | Positions of strain-specific variations |
|---|---|---|---|---|---|
| | A/T(1219), G/T(1268), C/G(1816), G/C(1849), A/G(2159) | | | | |

(*)for more details see FIG. 2.
a 23S rDNA sequenced in this work.
b partial (about 90%) sequences of whole *B. anthracis* Ames genome, data of TIGR (http://www.tigr.org).
c not sequenced, identified in this study by 16S/23S rRNA oligonucleotide microchip analysis (see Results).
d strains selected in this study as reference organisms to demonstrate subgroup identifications.
e need to be reexamined (see Results).
f final subgroup discrimination will be done after completion of 23S rRNA sequencing (see Results).
R = G, or A. Y = T, or C.
Subgroup-specific mutations, which are highlighted in bold, italics or underline denote mutations that are identical for two or more subgroups, and were grouped to demonstrate connections between different subgroups

TABLE 4

Degree of matching between oligonucleotide probes contained on microchip and the 16S and 23S rRNA sequences of eight reference microorganisms from the *B. cereus* group(*)

| | | Probe's target | | | | | | | | | | |
|---|---|---|---|---|---|---|---|---|---|---|---|---|
| | | B. thur + B. med all other | | | B. thur all other | | B.mycoides all other | | | | B. anthr. + B. myc all other | all other B. thur. B8 |
| Probes | Probe's name | ps1/ps2 | ps3/ps4 | ps5/ps6 | ps7/ps8 | ps9/ps10 | ps11/ps12 | ps13/ps14 | ps15/ps16 | ps19/ps20 | ps17/ps18 | ps21/ps22 |
| Reference organisms | *B. anthracis* AMES *B. thuringiensis* B8 (*B. anthracis* mimic) | +/− | +/− | +/− | +/− | +/− | +/− | +/− | +/− | +/− | +/− | +/− |
| | | +/− | +/− | +/− | +/− | +/− | +/− | +/− | +/− | +/− | +/− | −/+ |
| | *B. thuringiensis* 4Q281 | −/+ | −/+ | −/+ | −/+ | +/−2 | +/−2 | +/− | +/− | +/− | −/+ | p |
| | *B. cereus* T | +/− | +/− | +/− | +/− | +/− | +/− | +/− | +/− | +/− | −/+ | p |
| | *B. cereus* NCTC9620 | +/− | +/− | +/− | +/− | +/− | +/− | +/− | +/− | +/− | −/+ | p |
| | *B. medusa* ATCC25621 | −/+ | −/+ | −/+ | +/− | +/− | +/− | +/− | +/− | +/− | −/+ | p |
| | *B. mycoides* ATCC10206 | +/− | +/− | +/− | +/−3 | −/+ | −/+ | −/+ | −/+ | −/+ | −/+ | +/− |
| | *B. mycoides* ATCC6462m | +/− | +/− | +/− | +/−3 | −/+ | −/+ | −/+ | −/+ | −/+ | −/+ | +/− |

(*)data obtained from sequences of RNA genes for corresponding bacteria and represents the set of predicted signals after hybridization with labeled RNA from reference microorganisms.
+ denotes perfect matching
− denotes one mismatch
−2 denotes two mismatches
−3 denotes three mismatches
p denotes polymorphism
*B. thur*: *B. thuringiensis* 4Q281
*B. med*: *B. medusa* ATCC25621
*B. myc*: *B. mycoides* ATCC10206 and *B. mycoides* ATCC6462m
*B. anthr*: *B. anthracis* AMES
*B. thur*. B8: *B. thuringiensis* B8

TABLE 5

(SEQ ID NOS 57-121, respectively, in order of appearance)

| Title | Sequence | Target |
|---|---|---|
| 23F1 | TTT GGG CTA TGT TCC GTT TC | not Mycoides A, B |
| 23F2 | TTT GGG CTA GAT TCC GTT TC | Mycoides A, B |
| 23F5 | TAC GGG GTT GTT ACC CTC TA | not Mycoides A |
| 23F6 | TAC GGG GTT ATT ACC CTC TA | Mycoides A |
| 23F7 | CTA CGG GGT TGT TAC CCT CT | not Mycoides A |
| 23F8 | CTA CGG GGT TAT TAC CCT CT | Mycoides A |
| 23F5 | TAC GGG GTT GTT ACC CTC TA | not Mycoides A |
| 23F6 | TAC GGG GTT ATT ACC CTC TA | Mycoides A |
| 23F7 | CTA CGG GGT TGT TAC CCT CT | not Mycoides A |
| 23F8 | CTA CGG GGT TAT TAC CCT CT | Mycoides A |
| #54 | CGA ACG CGC CTT TCA ATT TC | not Mycoides B |
| SB25 | CGA AGC CGC CTT TGA ATT TC | Mycoides B |
| SB10 | GCC TTT CAA TTT CGA ACC AT | not Mycoides B |
| SB11 | GCC TTT GAA TTT CGC ACC AT | Mycoides B |
| A7 | CCC TCT ACG ACG GAC CTT TC | not Mycoides B |

TABLE 5-continued (SEQ ID NOS 57-121, respectively, in order of appearance)

| Title | Sequence | Target |
|---|---|---|
| A8 | CCC TCT GTG ACG AGC CTT TC | Mycoides B |
| 23F3 | TTT CCA GGT CGC TTC GTC TA | not Mycoides B |
| 23F4 | TTT CCA GGC TGC TTC GTC TA | Mycoides B |
| SB22 | TCT AGG GTT TTC AGA GGA TG | not

TABLE 6-continued

Preparation of Complex Buffers for Preparation of Micro-Matrices

| Buffer | Chemical/ Solvent/ Elementary buffer | Amount | Final Concentration | Comments |
|---|---|---|---|---|
| Stripping buffer | Guanidinium thiocyanate | 300 g | 4.9 M | Store solution at room temperature in a bottle with dark glass. Use for 20 stripping procedures (see below) then prepare a new portion. |
| | 1 M HEPES, pH 7.5 | 13.2 ml | 25 mM | |
| | 10% (w/v) Triton X-100 | 5.2 ml | 0.1% | |
| | Distilled water | 250 ml | | |

NOTE:
KEEP ALL BUFFERS IN BOTTLES WITH PLASTIC CAPS

TABLE 7

Materials and Equipment for Perparation of Micro-Matrices

| Chemicals/ Equipment | Manufacturer | Catalog # | Lot# |
|---|---|---|---|
| Acetone | Fisher | A18-4 | 11685 |
| Acrylamide/Bis (19/1) solution 40% | BioRad | 161-0144 | 66767 |
| 3-(Trimethoxysilyl)-propyl methacrylate | Aldrich | Z-6030 | 03915TI |
| Pyridine-borane complex | Aldrich | 17,975-2 | 13905MU |
| Glycerol | Sigma | G-7893 | 118H0280 |
| Methylene blue | Merck | 73881 | 51076 |
| Ethyl Alcohol (absolute, 200 proof | Aapec Alcohol and Chemical Co | N/A | 099I15UA |
| Chloroform | Aldrich | 31,998-8 | CO 09980AO |
| Repel Silane | Amersham-Pharmacia-Biotech | 39422 | 17-332-01 |
| Sodium borohydride | Aldrich | 21,346-2 | DU 00220MS |
| Sodium Hydroxide Solid | Sigma | S-5881 | 11K0116 |
| Sodium Periodate (meta) | Aldrich | S-1878 | 11K3644 |
| Sodium Phosphate, dibasic. anhydrous | Sigma | S-9763 | 119H0196 |
| Sodium Phosphate, monobasic monohydrate | Fisher | S-369 | 792237 |
| Sulfuric Acid | Fisher | A300-500 | 994173 |
| Sodium Dodecyl Sulfate | Sigma | L3771 | 83H08411 |
| SSPE, 20× (N-(5,6-di-O-iso-propylidene)hexyl acrylamide) | Sigma Argonne, custom made | S-2015 | 107H8508 |
| TEMED | Sigma | T-7024 | 67H0136 |
| Trifluoro-acetic Acid | Aldrich | T6,220-0 | 8K3483 |
| Filter (0.45 um filter unit); Millex-HV 0.4 | Millipore | SLHV 025 LS | |
| Glass slides, 3□ × 1□ Plain; | Corning | 2947 | |
| Mask | Nanoflim, California | | |
| Audio tape film | Radioshak XR 60; Type I | | |
| Clamp. Medium Binger clips | Masterbrand | BTM00252 | |
| Oriel Light Source | Oriel Instruments | 92532-1000 | S/N 139 |

DOCUMENTS

The following documents are incorporated by reference to the extent they enable the present invention:

Amann, R. I., W. Ludwig, and K.-H. Schleifer. 1995. Phylogenetic identification and in situ detection of individual microbial cells without cultivation. Microbiol. Rev. 59:143-169.

Andersen, G. L., J. M. Simchock, and K. H. Wilson. 1996. Identification of a region of genetic variability among *Bacillus anthracis* strains and related species. J. Bacteriol. 178:377-384.

Aronson, A. I. 1993. Insecticidal toxins, p. 953-963. In A. B. Sonenshein, J. A. Hoch, and R. Losick (ed), *Bacillus subtilis* and other gram-positive bacteria: biochemistry, physiology, and molecular genetics. American Society for Microbiology, Washington, D.C Aronson, A. I., W. Beckman, and P. Dunn. 1986. *Bacillus thuringiensis* and related insect pathogens. Microbiol. Rev. 50:1-24.

Ash, C., and M. D. Collins. 1992. Comparative analysis of 23S ribosomal RNA gene sequences of *Bacillus anthracis* and emetic *Bacillus cereus* determined by PCR-directsequencing. FEMS Microbiol. Lett. 94:75-80.

Ash, C., J. A. E. Farrow, M. Dorsch, E. Stackebrandt, and M. D. Collins. 1991. Comparative analysis of *Bacillus anthracis, Bacillus cereus*, and related species on the basis of reverse transcriptase sequencing of 16S rRNA. Int. J. Syst. Bacteriol. 41:343-346.

Ash, C., J. A. E. Farrow, W. Wallbanks, and M. D. Collins. 1991. Phylogenetic heterogeneity of the genus *Bacillus* revealed by comparative analysis of small-subunit-ribosomal RNA sequences. Lett. Appl. Microbiol. 13:202-206.

Barsky, I., A. Grammatin, A. Ivanov, E. Kreindlin, E. Kotova, V. Barsky, and A. D. Mirzabekov. 1998. Luminescent image analyzers of biological microchips. J. Opt. Technol. (Russian). 65:83-87.

Bavykin, S. G., J. P. Akowski, V. M. Zakhariev, V. E. Barsky, A. N. Perov and A. D. Mirzabekov. 2001. Portable system for microbial sample preparation and oligonucleotide microarray analysis. Appl. Environ. Microbiol., 67: 922-928.

Beyer, W., P. Glöckner, J. Otto, and R. Böhm. 1996. A nested PCR and DNA-amplification-fingerprinting method for detection and identification of *Bacillus anthracis* in soil samples from former tanneries. Salisbury Medical Bulletin, Special Supplement No. 87:47-49.

Beyer, W., S. Pocivalsek, and R. Böhm. 1999. Polymerase chain reaction-ELISA to detect *Bacillus anthracis* from soil samples—limitations of present published primers. J. Appl. Microbiol. 87:229-236.

Boom, R., C. J. Sol, M. M. Salimans, C. L. Jansen, P. M. Wertheim-van Dillen, and J. van der Noordaa. 1990. Rapid and simple method for purification of nucleic acids. J. Clin. Microbiol. 28:495-503.

Chee, M., R. Yang, E. Hubbrll, A. Berno, X. C. Huang, D. Stern, J. Winkler, D. J. Lockhart, M. S. Morris, and S. P. A. Fodor. 1996. Accessing genetic information with high-density DNA arrays. Science 274: 610-614.

Daffonchio, D., A. Cherif, and S. Borin. 2000. Homoduplex and heteroduplex polymorphisms of the amplified ribosomal 16S-23S internal transcribed spacers describe genetic relationships in the "*Bacillus cereus* Group." Appl. Environ. Microbiol. 66:5460-5468.

Delaporte, de M. 1969. Description de *Bacillus medusa* n.sp. C. R. Acad. Sc. Paris 269 (Serie D): 1129-1131.

Drobniewski, F. A. 1993. *Bacillus cereus* and related species, p. 324-338. In Clinical microbiology reviews, Vol. 6. American Society for Microbiology, Washington, D.C.

Ezzell, J. W. Jr., T. G. Abshire, S. F. Little, B. C. Lidgerding, and C. Brown. 1990. Identification of *Bacillus anthracis* by using monoclonal antibody to cell wall galactose-Nacetylglucosamine polysaccharide. J. Clin. Microbiol. 28:223-231.

Fox, A., G. E. Black, K. Fox, and S. Rostovtseva. 1993. Determination of carbohydrate profiles of *Bacillus anthracis* and *Bacillus cereus* including identification of O-methyl methylpentoses by using gas chromatography-mass spectrometry. J. Clin. Microbiol. 31:887-894.

Giffel, M. C., R. R. Beumer, N. Klijn, A. Wagendorp, and F. M. Rombouts. 1997. Discrimination between *Bacillus cereus* and *Bacillus thuringiensis* using specific DNA probes based in variable regions of 16S rRNA. FEMS Microbiol. Lett. 146:47-51.

Gonzalez Jr., J. M., B. J. Brown, and B. C. Carlton. 1982. Transfer of *Bacillus thuringiensis* plasmids coding for β-endotoxin among strains of *B. thuringiensis* and *B. cereus*. Proc. Natl. Acad. Sci. USA 79:6951-6955.

Guschin, D., G. Yershov, A. Zaslavsky, A. Gemmell, V. Shick, D. Proudnikov, P. Arenkov, and A. Mirzabekov. 1997. Manual manufacturing of oligonucleotide, DNA, and protein microchips. Anal. Biochem. 250:203-211.

Guschin, D. Y., B. K. Mobarry, D. Proudnikov, D. A. Stahl, B. E. Rittmann, and A. D. Mirzabekov. 1997. Oligonucleotide microchips as genosensors for determinative and environmental studies in microbiology. Appl. Environ. Microbiol. 63: 2397-2402.

Harrell, L. J., G. L. Andersen, and K. H. Wilson. 1995. Genetic variability of *Bacillus anthracis* and related species. J. Clin Microbiol. 33:1847-1850.

Helgason, E., O. A. Økstad, D. A. Caugant, H. A. Johansen, A. Fouet, M. Mock, I. Hegna, and A.-B. Kolsto. 2000. *Bacillus anthracis, Bacillus cereus*, and *Bacillus thuringiensis*—one species on the basis of genetic evidence. Appl. Environ. Microbiol. 66:2627-2630.

Henderson, I. 1996. Fingerprinting *Bacillus anthracis* strains. Salisbury Medical Bulletin, Special Supplement No. 87:55-58.

Henderson, I., C. J. Duggleby, and P. C. B. Turnbull. 1994. Differentiation of *Bacillus anthracis* from other *Bacillus cereus* group bacteria with the PCR. Int. J. Syst. Bacteriol. 44:99-105.

Henderson, I., Y. Dongzheng, and P. C. B. Turnbull. 1995. Differentiation of *Bacillus anthracis* and other *Bacillus cereus* group' bacteria using IS231-derived sequences. FEMS Microbiol. Lett. 128:113-118.

Hutson, R. A., C. J. Duggleby, J. R. Lowe, R. J. Manchee, and P. C. B. Turnbull. 1993. The development and assessment of DNA and oligonucleotide probes for the specific detection of *Bacillus anthracis*. J. Appl. Bacteriol. 75:463-472.

Jackson, P. J., K. K. Hill, M. T. Laker, L. O. Ticknor, and P. Keim. 1999. Genetic comparison of *Bacillus anthracis* and its close relatives using amplified fragment length polymorphism and polymerase chain reaction analysis. J. Appl. Microbiol. 87:263-269.

Kiem, P., A. Kalif, J. Schupp, K. Hill, S. E. Travis, K. Richmond, D. M. Adair, M. Hugh-Jones, C. R. Kuske, and P. Jackson. 1997. Molecular evolution and diversity in *Bacillus anthracis* as detected by amplified fragment length polymorphism markers. J. Bacteriol. 179:818-824.

Lander, E. S. 1999. Array of hope. Nature Genet. 21(suppl.):3-4.

Lane, D. J. 1991. 16S/23S rRNA sequencing, p. 115-176. In E. Stackenbrandt and M. Goodfellow (ed.), Nucleic acid techniques in bacterial systematics, John Wiley & Sons, City, State.

Lechner, S., R. Mayr, K. P. Fransis, B. M. Prub, T. Kaplan, E. Wiebner-Gunkel, G. S. Stewart, and A. B. Scherer. 1998. *Bacillus weihenstephanensis* sp. nov. is a new psychrotolerant species of the *Bacillus cereus* group. Int. J. Syst. Bacteriol. 48:1373-1382.

Lee, M. A., G. Brightwell, D. Leslie, H. Bird, and A. Hamilton. 1999. Fluorescent detection techniques for real-time multiplex strand specific detection of *Bacillus anthracis* using rapid PCR. J. Appl. Microbiol. 87:218-223.

Liang, X., and D. Yu. 1999. Identification of *Bacillus anthracis* strains in China. J. Appl. Microbiol. 87:200-203.

Longchamp, P., and T. Leighton. 1999. Molecular recognition specificity of *Bacillus anthracis* spore antibodies. J. Appl. Microbiol. 87:246-249.

Nakamura, L. K., and M. A. Jackson. 1995. Clarification of the taxonomy of *Bacillus mycoides*. Int. J. Syst. Bacteriol. 45:46-49.

Nakamura, L. K. 1998. *Bacillus pseudomycoides* sp. nov. Int. Syst. Bacteriol. 48:1031-1034.

Patra, G., P. Sylvestre, V. Ramisse, J. Therasse, and J. L. Guesdon. 1996. DNA fingerprinting of *Bacillus anthracis* strains. Salisbury Medical Bulletin, Special Supplement No. 87:59.

Patra, G., P. Sylvestre, V. Ramisse, J. Therasse, and J.-L. Guesdon. 1996. Isolation of a specific chromosomic DNA sequence of *Bacillus anthracis* and its possible use in diagnosis. FEMS Immunol. Med. Microbiol. 15:223-231.

Priest, F. G., D. A. Kaji, Y. B. Rosato, and V. P. Canhos. 1994. Characterization of *Bacillus thuringiensis* and related bacteria by ribosomal RNA gene restriction fragment length polymorphisms. Microbiology 140:1015-1022.

Proudnikov, D., E. Timofeev, and A. Mirzabekov. 1998. Immobilization of DNA in polyacrylamide gel for the manufacture of DNA and DNA-oligonucleotide microchips. Anal. Biochem. 259:34-41.

Prub, B. M., K. P. Francis, F. von Stetten, and S. Scherer. 1999. Correlation of 16S ribosomal DNA signature sequences with temperature-dependent growth rates of Mesophilic and Psychrotolerant strains of the *Bacillus cereus* group. J. Bacteriol. 181:2624-2630.

Ramisse, V., G. Patra, H. Garrigue, J.-L. Guesdon, and M. Mock. 1996. Identification and characterization of *Bacillus anthracis* by multiplex PCR analysis of sequences on plasmids pXO1 and pXO2 and chromosomal DNA. FEMS Microbiol. Lett. 145:9-16.

Ryzhov, V., Y. Hathout, and C. Fenselau. 2000. Rapid characterization of spores of *Bacillus cereus* group bacteria by matrix-assisted laser desorption-ionization time-of-flight mass spectrometry. Appl Environ. Microbiol. 66:3828-3834.

Shangkuan, Y.-H., J.-F. Yang, H.-C. Lin, and M.-F. Shaio. 2000. Comparison of PCR-RFLP, ribotyping and ERIC-PCR for typing *Bacillus anthracis* and *Bacillus cereus* strains. J. Appl. Microbiol. 89:452-462.

Sj'stedt, A., U. Eriksson, V. Ramisse, and H. Garrigue. 1996. Detection of the vegetative form of *Bacillus anthracis* in soil by PCR. Salisbury Medical Bulletin, Special Supplement No. 87, 50.

Sneath, P. H. A. 1986. Endospore-forming Gram-positive rods and cocci, p. 1104-1139. In J. G. Holt (ed.), Bergey's Manual of Systematic Bacteriology The Williams & Wilkins Co., Baltimore, Md.

Stahl, D. A. and R. Amann. 1991. Development and application of nucleic acid probes in bacterial systematics, p. 205-248. In E. Stackebrandt and M. Goodfellow (ed.), Sequencing and hybridization techniques in bacterial systematics. John Wiley and Sons, Chichester, England.

Strizhkov, B. N., A. L. Drobyshev, V. M. Mikhailovich, and A. D. Mirzabekov. 2000. PCR amplification on a microarray of gel-immobilized oligonucleotides: detection of bacterial toxin- and drug-resistant genes and their mutations. BioTechniques 29:844-857.

Timofeev, E. N., S. V. Kochetkova, A. D. Mirzabekov and V. L. Florentiev. 1996. Regioselective immobilization of short oligonucleotides to acrylic copolymer gels. Nucl. Acids Res. 24: 3142-3148.

Thorne, C. B. 1985. Genetics of *Bacillus anthracis*, p. 56-62. In L. Leive (ed.), Microbiology-1985. American Society for Microbiology, Washington, D.C.

Turnbull, P. C. B. 1999. Definitive identification of *Bacillus anthracis*—a review. J. Appl. Microbiol. 87:237-240.

Turnbull, P. C. B., R. A. Hutson, M. J. Ward, M. N. Jones, C. P. Quinn, N.J. Finnie, C. J. Duggleby, J. M. Kramer, and J. Melling. 1992. *Bacillus anthracis* but not always anthrax. J. Appl. Bacteriol. 72; 21-28.

Woese, C. R. 1987. Bacterial evolution. Microbiol. Rev. 51:221-271.

Wunschel, D., K. F. Fox, G. E. Black, and A. Fox. 1994. Discrimination among the *Bacillus cereus* group, in comparison to *B. subtilis*, by structural carbohydrate profiles and ribosomal RNA spaser region PCR. Syst. Appl. Microbiol. 17:625-635.

Yamakama, I., D. Nakajama, and O. Ohara. 1996. Identification of sequence motifs causing band compressions on human cDNA sequencing. DNA Research 3:81-86.

Yershov, G., V. Barsky, A. Belgovskiy, Eu. Kirillov, E. Kreindlin, I. Ivanov, S. Parinov, D. Guschin, A. Drobyshev, S. Dubiley, and A. Mirzabekov. 1996. DNA analysis and diagnostics on oligonucleotide microchips. Proc. Natl. Acad. Sci. USA. 93:4913-4918.

Zlatanova, J., and A. D. Mirzabekov. 2001. Gel immobilized microarrays of nucleic acids and proteins. In J. B. Rampal (ed.), Methods in Molecular Biology: DNA Arrays, Methods, and Protocols, in press, Human Press, Inc., Totowa, N.J.

---

We claim:

1. A method for detecting an isolate of *Bacillus anthracis* in a sample, the method comprising:
   (a) placing on a microchip a set of oligonucleotide probes targeted to rRNA sequences, wherein the set of oligonucleotide probes comprises the probe sequences as set forth in
   (i) TTT GGG CTA TGT TCC GTT TC (SEQ ID NO: 57)
   (ii) TTT GGG CTA GAT TCC GTT TC (SEQ ID NO: 58)
   (iii) CAG CTC AGC CTT CAC GAT AA (SEQ ID NO: 97)
   (iv) CAG CTC AGC CTT TAC GAT AA (SEQ ID NO: 98)

(v) TCT AGG GTT GTC AGA GGA TG (SEQ ID NO: 76)
(vi) TCT AGG GTT TTC AGA GGA TG (SEQ ID NO: 75)
(vii) CCG CTA ACT TCA TAA GAG CA (SEQ ID NO: 103)
(viii) CCG CTA ACT TCT TGA GAG CA (SEQ ID NO: 104)
(ix) reverse complement of GCTTCTCCTTCGGGAG-CAGA (SEQ ID NO: 19);
(x) reverse complement of GCTTCcCCT-TCGGGgGCAGA (SEQ ID NO: 20); and
(xi) CCC TCT GTG ACG AGC CTT TC (SEQ ID NO: 72)

and discriminates among the *B. cereus* subgroups;
(b) providing conditions for hybridization of the probes with nucleic acids from the sample; and
(c) analyzing hybridization signals in the microchip to detect *Bacillus anthracis*.

2. The method of claim 1, wherein the oligonucleotide probes are directed to 16S rRNA and 23 S rRNA.

3. The method of claim 1, wherein the nucleic acids are labeled.

4. The method of claim 3, wherein the labels are fluorescent dyes.

5. The method of claim 1, wherein oligonucleotide probes comprising sequences designated by SEQ ID NOS: 75 and 76 discriminate subgroups *Anthracis, Cereus* A and *Mycoides* B from subgroups *Cereus* B, *Thuringiensis* A, B and *Mycoides* A.

6. The method of claim 1, wherein oligonucleotide probes targeted to nucleic acid sequences set forth in SEQ ID NOS: 103-104 discriminate subgroup *Thuringiensis* B from other subgroups of *B. cereus* group.

7. The method of claim 1, wherein the oligonucleotide probes targeted to nucleic acid sequences as set forth in SEQ ID NOS: 97-98 discriminate subgroups *Anthracis, Thuringiensis* B and *Mycoides* from subgroups *Cereus* A, B.

8. The method of claim 1, wherein the oligonucleotide probes targeted to nucleic acid sequences as set forth in SEQ ID NOS: 57-58 discriminate *Mycoides* A, B from subgroups *Anthracis, Cereus* A, B and *Thuringiensis* B.

9. A method for taxonomically classifying *B. cereus* group, said method comprising:
(a) placing on a microchip a set of oligonucleotide probes targeted to rRNA sequences, wherein the set of oligonucleotide probes comprises the probe sequences as set forth in
(i) TTT GGG CTA TGT TCC GTT TC (SEQ ID NO: 57)
(ii) TTT GGG CTA GAT TCC GTT TC (SEQ ID NO: 58)
(iii) CAG CTC AGC CTT CAC GAT AA (SEQ ID NO: 97)
(iv) CAG CTC AGC CTT TAC GAT AA (SEQ ID NO: 98)
(v) TCT AGG GTT GTC AGA GGA TG (SEQ ID NO: 76)
(vi) TCT AGG GTT TTC AGA GGA TG (SEQ ID NO: 75)
(vii) CCG CTA ACT TCA TAA GAG CA (SEQ ID NO: 103)
(viii) CCG CTA ACT TCT TGA GAG CA (SEQ ID NO: 104)
(ix) reverse complement of GCTTCTCCTTCGGGAG-CAGA (SEQ ID NO: 19);
(x) reverse complement of GCTTCcCCT-TCGGGgGCAGA (SEQ ID NO: 20); and
(xi) CCC TCT GTG ACG AGC CTT TC (SEQ ID NO: 72)
for *B. cereus* group isolates; and
(b) using the signature profiles of 16S and 23S rRNA sequences and phylogenetic trees to classify the various *B. cereus* group isolates.

* * * * *

UNITED STATES PATENT AND TRADEMARK OFFICE
CERTIFICATE OF CORRECTION

| | | |
|---|---|---|
| PATENT NO. | : 7,288,371 B1 | Page 1 of 1 |
| APPLICATION NO. | : 10/287455 | |
| DATED | : October 30, 2007 | |
| INVENTOR(S) | : Bavykin et al. | |

It is certified that error appears in the above-identified patent and that said Letters Patent is hereby corrected as shown below:

On the title page, item (73), Assignee should read:

--UCHICAGO ARGONNE LLC--

Signed and Sealed this

Twenty-first Day of October, 2008

JON W. DUDAS
*Director of the United States Patent and Trademark Office*

SEQUENCE LISTING

```
<160> NUMBER OF SEQ ID NOS: 166

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gagcgaatgg attaagagct                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gagcgaatgg attgagagct                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agcttgctct tatgaagtta                                                    20

<210> SEQ ID NO 4
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 4
agcttgctct caagaagtta                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgctcttatg aagttagcgg                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgctctcaag aagttagcgg                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cattttgaac cgcatggttc                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cattttgaac tgcatggttc                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cattttgaac cgcatggttc                                               20

<210> SEQ ID NO 10
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 10
cattttgcac cgcatggtgc                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaccgcatgg ttcgaaattg                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caccgcatgg tgcgaaattc                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atggttcgaa attgaaaggc                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atggtgcgaa attcaaaggc                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gaaattgaaa ggcggcttcg                                                    20

<210> SEQ ID NO 16
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 16
gaaattcaaa ggcggcttcg                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
catcctctga caaccctaga                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
catcctctga aaaccctaga                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcttctcctt cgggagcaga                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcttcccctt cgggggcaga                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttatcgtgaa ggctgagctg                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 22
ttatcgtaaa ggctgagctg                                          20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgataccaat ggtatcagtg                                          20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgataccgaa tggtatcagt g                                        21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cggtcttgca gctctttgta                                          20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
attccagctt cacgcagtc                                           19

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 27
gtttgatcct ggctcag                                             17

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 28

```
ccagtcttat gggcaggtta c                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 29
tccataagtg acagccgaag c                                              21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 30
ctacgggagg cagcagtggg                                                20

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 31
gwattaccgc ggckgctg                                                  18

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 32
ggattagata ccctggtagt                                                20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 33
ccgtcaattc ctttragttt                                                20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 34
ttcgggagca gagtgacagg t                                              21

<210> SEQ ID NO 35
<211> LENGTH: 21
<212> TYPE: DNA
```

```
<213> ORGANISM: Artificial Sequence
<220> FEATURE:
<223> OTHER INFORMATION: Description of Artificial Sequence: Primer

<400> SEQUENCE: 35
tacacaccgc ccgtcacacc a                                              21

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 36
rgtgagctrt tacgc                                                     15

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 37
ccgaatgggg vaaccc                                                    16

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 38
ccgtttcgct cgccgctact c                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 39
tagtgatcga tagtgaacca g                                              21

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 40
cattmtacaa aaggyacgc                                                 19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 41
gcgtrccttt tgtakaatg                                                 19
```

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 42
tagtgatcga tagtgaacca g                                       21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 43
tagtgatcga tagtgaacca g                                       21

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 44
rgtgagctrt tacgc                                              15

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 45
wgcgtaayag ctcac                                              15

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 46
cataccggca ttctcacttc                                         20

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 47
acaggcgtag gcgatggac                                          19

<210> SEQ ID NO 48
<211> LENGTH: 17
<212> TYPE: DNA
<213> ORGANISM: Artificial Sequence
<220> FEATURE:

<223> OTHER INFORMATION: Description of Artificial Sequence: Primer

<400> SEQUENCE: 48
aacctttggg cgcctcc                                                              17

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 49
cyacctgtgw cggttt                                                               16

<210> SEQ ID NO 50
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 50
aaaccgwcac aggtrg                                                               16

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 51 caygggtct ttrcgtc                                                               17

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 52
gacgyaaaga ccccrtg                                                              17

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 53
gagycgacat cgagg                                                                15

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 54
cctcgatgtc grctc                                                                15

```
<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 55
gyttagatgc yttc                                                        14

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 56
ggcggcgtcc tactctcac                                                   19

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 57
tttgggctat gttccgtttc                                                  20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 58
tttgggctag attccgtttc                                                  20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 59
tacggggttg ttaccctcta                                                  20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 60
tacggggtta ttaccctcta                                                  20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Primer
```

```
<400> SEQUENCE: 61
ctacggggtt gttaccctct                                          20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 62
ctacggggtt attaccctct                                          20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 63
tacggggttg ttaccctcta                                          20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 64
tacggggtta ttaccctcta                                          20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 65
ctacggggtt gttaccctct                                          20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 66
ctacggggtt attaccctct                                          20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 67
cgaagccgcc tttcaatttc                                          20

<210> SEQ ID NO 68
<211> LENGTH: 20
```

```
<212> TYPE: DNA
<213> ORGANISM: Artificial Sequence
<220> FEATURE:
<223> OTHER INFORMATION: Description of Artificial Sequence: Primer

<400> SEQUENCE: 68
cgaagccgcc tttgaatttc                                                    20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 69
gcctttcaat ttcgaaccat                                                    20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 70
gcctttgaat ttcgcaccat                                                    20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 71
ccctctacga cggacctttc                                                    20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 72
ccctctgtga cgagcctttc                                                    20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 73
tttccaggtc gcttcgtcta                                                    20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 74
```
tttccaggct gcttcgtcta                                                20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 75
tctagggttt tcagaggatg                                                20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 76
tctagggttg tcagaggatg                                                20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 77
ccggtttcaa aggctcccgc                                                20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 78
ccggcttcaa tggctcccgc                                                20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 79
gacccctagt ccaatcagtg                                                20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 80
gacccctagt tcaatcagtg                                                20

<210> SEQ ID NO 81
<211> LENGTH: 20
<212> TYPE: DNA
<213> ORGANISM: Artificial Sequence -continued

```
<220> FEATURE:
<223> OTHER INFORMATION: Description of Artificial Sequence: Primer

<400> SEQUENCE: 81
tggtatcaat ccgcagcttc                                                 20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 82
tggtatcaat tcgcagcttc                                                 20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 83
acttctaagc actccaccag                                                 20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 84
acttctaagc gctccaccag                                                 20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 85
tcacttctaa gcactccacc                                                 20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 86
tcacttctaa gcgctccacc                                                 20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 87
atgtattcag ataaggatac                                                 20
```

```
<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 88
atgtattcag gtaaggatac                                          20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 89
ataccattgg tatcaatccg                                          20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 90
taccattcgg tatcaatccg                                          20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 91
taccattggt atcaatccgc                                          20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 92
accattcggt atcaatccgc                                          20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 93
cactgatacc attggtatca                                          20

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Primer
```

<400> SEQUENCE: 94
cactgatacc attcggtatc a                                              21

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 95
gctcagcctt cacgataagc                                                20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 96
gctcagcctt tacgataagc                                                20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 97
cagctcagcc ttcacgataa                                                20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 98
cagctcagcc tttacgataa                                                20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 99
gaaccatgcg gttcaaaatg                                                20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 100
gaaccatgca gttcaaaatg                                                20

<210> SEQ ID NO 101

```
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 101
taacttcata agagcaagct                                                    20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 102
taacttcttg agagcaagct                                                    20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 103
ccgctaactt cataagagca                                                    20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 104
ccgctaactt cttgagagca                                                    20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 105
agctcttaat ccattcgctc                                                    20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 106
agctctcaat ccattcgctc                                                    20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 107
```

```
cattacgtat ggtgggtttc                                              20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 108
cattacgtat agtgggtttc                                              20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 109
atgtattcag ataaggatac                                              20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 110
atgtattcag gtaaggatac                                              20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 111
tctgtcttcc ttaccctatg                                              20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 112
tctgtcttcc ataccctatg                                              20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 113
gccatcaccc gttaacgggc                                              20

<210> SEQ ID NO 114
<211> LENGTH: 20
<212> TYPE: DNA
```

```
<213> ORGANISM: Artificial Sequence
<220> FEATURE:
<223> OTHER INFORMATION: Description of Artificial Sequence: Primer

<400> SEQUENCE: 114
gccatcaccc attaacgggc                                                    20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 115
acgccatcac ccgttaacgg                                                    20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 116
acgccatcac ccattaacgg                                                    20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 117
caactagcac ttgttcttcc                                                    20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 118
cggtcttgca gctctttgta                                                    20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 119
acagatttgt gggattggct                                                    20

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 120
attccagctt cacgcagtc                                                     19
```

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 121
gatgatgatg atgatgatga                                              20

<210> SEQ ID NO 122
<211> LENGTH: 18
<212> TYPE: DNA
<213> ORGANISM: Bacillus anthracis

<400> SEQUENCE: 122
taagagcttg ctcttatg                                                18

<210> SEQ ID NO 123
<211> LENGTH: 18
<212> TYPE: DNA
<213> ORGANISM: Bacillus cereus

<400> SEQUENCE: 123
taagagcttg ctcttatg                                                18

<210> SEQ ID NO 124
<211> LENGTH: 18
<212> TYPE: DNA
<213> ORGANISM: Bacillus cereus

<400> SEQUENCE: 124
taagagcttg ctcttatg                                                18

<210> SEQ ID NO 125
<211> LENGTH: 18
<212> TYPE: DNA
<213> ORGANISM: Bacillus thuringiensis

<400> SEQUENCE: 125
taagagcttg ctcttatg                                                18

<210> SEQ ID NO 126
<211> LENGTH: 18
<212> TYPE: DNA
<213> ORGANISM: Bacillus thuringiensis

<400> SEQUENCE: 126
tgagagcttg ctctcaag                                                18

<210> SEQ ID NO 127
<211> LENGTH: 18
<212> TYPE: DNA
<213> ORGANISM: Bacillus mycoides

<400> SEQUENCE: 127
taagagcttg ctcttatg                                                18

<210> SEQ ID NO 128
<211> LENGTH: 18
<212> TYPE: DNA
<213> ORGANISM: Bacillus mycoides

```
<400> SEQUENCE: 128
taagagcttg ctctttatg                                              18

<210> SEQ ID NO 129
<211> LENGTH: 30
<212> TYPE: DNA
<213> ORGANISM: Bacillus anthracis

<400> SEQUENCE: 129
aacattttga accgcatggt tcgaaattga                                  30

<210> SEQ ID NO 130
<211> LENGTH: 30
<212> TYPE: DNA
<213> ORGANISM: Bacillus cereus

<400> SEQUENCE: 130
aacattttga accgcatggt tcgaaattga                                  30

<210> SEQ ID NO 131
<211> LENGTH: 30
<212> TYPE: DNA
<213> ORGANISM: Bacillus cereus

<400> SEQUENCE: 131
aacattttga accgcatggt tcgaaattga                                  30

<210> SEQ ID NO 132
<211> LENGTH: 30
<212> TYPE: DNA
<213> ORGANISM: Bacillus thuringiensis

<400> SEQUENCE: 132
aacattttga actgcatggt tcgaaattga                                  30

<210> SEQ ID NO 133
<211> LENGTH: 30
<212> TYPE: DNA
<213> ORGANISM: Bacillus thuringiensis

<400> SEQUENCE: 133
aacattttga actgcatggt tcgaaattga                                  30

<210> SEQ ID NO 134
<211> LENGTH: 30
<212> TYPE: DNA
<213> ORGANISM: Bacillus mycoides

<400> SEQUENCE: 134
aatattttga actgcatagt tcgaaattga                                  30

<210> SEQ ID NO 135
<211> LENGTH: 30
<212> TYPE: DNA
<213> ORGANISM: Bacillus mycoides

<400> SEQUENCE: 135
aacattttgc accgcatggt gcgaaattca                                  30

<210> SEQ ID NO 136
<211> LENGTH: 33
<212> TYPE: DNA
<213> ORGANISM: Bacillus anthracis
```

```
<400> SEQUENCE: 136
acaaccctag agatagggct tctccttcgg gag                              33

<210> SEQ ID NO 137
<211> LENGTH: 33
<212> TYPE: DNA
<213> ORGANISM: Bacillus cereus

<400> SEQUENCE: 137
acaaccctag agatagggct tctccttcgg gag                              33

<210> SEQ ID NO 138
<211> LENGTH: 33
<212> TYPE: DNA
<213> ORGANISM: Bacillus cereus

<400> SEQUENCE: 138
aaaaccctag agatagggct tctccttcgg gag                              33

<210> SEQ ID NO 139
<211> LENGTH: 33
<212> TYPE: DNA
<213> ORGANISM: Bacillus thuringiensis

<400> SEQUENCE: 139
aaaaccctag agatagggct tctccttcgg gag                              33

<210> SEQ ID NO 140
<211> LENGTH: 33
<212> TYPE: DNA
<213> ORGANISM: Bacillus thuringiensis

<400> SEQUENCE: 140
aaaaccctag agatagggct tctccttcgg gag                              33

<210> SEQ ID NO 141
<211> LENGTH: 33
<212> TYPE: DNA
<213> ORGANISM: Bacillus mycoides

<400> SEQUENCE: 141
aaaactctag agatagagct tctccttcgg gag                              33

<210> SEQ ID NO 142
<211> LENGTH: 33
<212> TYPE: DNA
<213> ORGANISM: Bacillus mycoides

<400> SEQUENCE: 142
acaaccctag agatagggct tccccttcgg ggg                              33

<210> SEQ ID NO 143
<211> LENGTH: 18
<212> TYPE: DNA
<213> ORGANISM: Bacillus anthracis

<400> SEQUENCE: 143
taagagcttg ctcttatg                                              18

<210> SEQ ID NO 144
<211> LENGTH: 18
<212> TYPE: DNA
```

```
<213> ORGANISM: Bacillus thuringiensis

<400> SEQUENCE: 144
taagagcttg ctcttatg                                            18

<210> SEQ ID NO 145
<211> LENGTH: 18
<212> TYPE: DNA
<213> ORGANISM: Bacillus cereus

<400> SEQUENCE: 145
taagagcttg ctcttatg                                            18

<210> SEQ ID NO 146
<211> LENGTH: 18
<212> TYPE: DNA
<213> ORGANISM: Bacillus cereus

<400> SEQUENCE: 146
taagagcttg ctcttatg                                            18

<210> SEQ ID NO 147
<211> LENGTH: 18
<212> TYPE: DNA
<213> ORGANISM: Bacillus thuringiensis

<400> SEQUENCE: 147
tgagagcttg ctctcaag                                            18

<210> SEQ ID NO 148
<211> LENGTH: 18
<212> TYPE: DNA
<213> ORGANISM: Bacillus medusa

<400> SEQUENCE: 148
tgagagcttg ctctcaag                                            18

<210> SEQ ID NO 149
<211> LENGTH: 18
<212> TYPE: DNA
<213> ORGANISM: Bacillus mycoides

<400> SEQUENCE: 149
taagagcttg ctcttatg                                            18

<210> SEQ ID NO 150
<211> LENGTH: 18
<212> TYPE: DNA
<213> ORGANISM: Bacillus mycoides

<400> SEQUENCE: 150
taagagcttg ctcttatg                                            18

<210> SEQ ID NO 151
<211> LENGTH: 30
<212> TYPE: DNA
<213> ORGANISM: Bacillus anthracis

<400> SEQUENCE: 151 aacatttga accgcatggt tcgaaattga                                30

<210> SEQ ID NO 152
<211> LENGTH: 30
```

-continued

<212> TYPE: DNA
<213> ORGANISM: Bacillus thuringiensis

<400> SEQUENCE: 152
aacattttga accgcatggt tcgaaattga 30

<210> SEQ ID NO 153
<211> LENGTH: 30
<212> TYPE: DNA
<213> ORGANISM: Bacillus cereus

<400> SEQUENCE: 153
aacattttga accgcatggt tcgaaattga 30

<210> SEQ ID NO 154
<211> LENGTH: 30
<212> TYPE: DNA
<213> ORGANISM: Bacillus cereus

<400> SEQUENCE: 154
aacattttga accgcatggt tcgaaattga 30

<210> SEQ ID NO 155
<211> LENGTH: 30
<212> TYPE: DNA
<213> ORGANISM: Bacillus thuringiensis

<400> SEQUENCE: 155
aacattttga actgcatggt tcgaaattga 30

<210> SEQ ID NO 156
<211> LENGTH: 30
<212> TYPE: DNA
<213> ORGANISM: Bacillus medusa

<400> SEQUENCE: 156
aacattttga accgcatggt tcgaaattga 30

<210> SEQ ID NO 157
<211> LENGTH: 30
<212> TYPE: DNA
<213> ORGANISM: Bacillus mycoides

<400> SEQUENCE: 157
aacattttgc accgcatggt gcgaaattca 30

<210> SEQ ID NO 158
<211> LENGTH: 30
<212> TYPE: DNA
<213> ORGANISM: Bacillus mycoides

<400> SEQUENCE: 158
aacattttgc accgcatggt gcgaaattca 30

<210> SEQ ID NO 159
<211> LENGTH: 33
<212> TYPE: DNA
<213> ORGANISM: Bacillus anthracis

<400> SEQUENCE: 159
acaaccctag agatagggct tctccttcgg gag 33

<210> SEQ ID NO 160

```
<211> LENGTH: 33
<212> TYPE: DNA
<213> ORGANISM: Bacillus thuringiensis

<400> SEQUENCE: 160
acaaccctag agatagggct tctccttcgg gag                               33

<210> SEQ ID NO 161
<211> LENGTH: 33
<212> TYPE: DNA
<213> ORGANISM: Bacillus cereus

<400> SEQUENCE: 161
aaaaccctag agatagggct tctccttcgg gag                               33

<210> SEQ ID NO 162
<211> LENGTH: 33
<212> TYPE: DNA
<213> ORGANISM: Bacillus cereus

<400> SEQUENCE: 162
aaaaccctag agatagggct tctccttcgg gag                               33

<210> SEQ ID NO 163
<211> LENGTH: 33
<212> TYPE: DNA
<213> ORGANISM: Bacillus thuringiensis

<400> SEQUENCE: 163
aaaaccctag agatagggct tctccttcgg gag                               33

<210> SEQ ID NO 164
<211> LENGTH: 33
<212> TYPE: DNA
<213> ORGANISM: Bacillus medusa

<400> SEQUENCE: 164
aaaaccctag agatagggct tctccttcgg gag                               33

<210> SEQ ID NO 165
<211> LENGTH: 33
<212> TYPE: DNA
<213> ORGANISM: Bacillus mycoides

<400> SEQUENCE: 165
acaaccctag agatagggct tccccttcgg ggg                               33

<210> SEQ ID NO 166
<211> LENGTH: 33
<212> TYPE: DNA
<213> ORGANISM: Bacillus mycoides

<400> SEQUENCE: 166
acaaccctag agatagggct tccccttcgg ggg                               33
```